US010774371B2

(12) United States Patent
Sun et al.

(10) Patent No.: US 10,774,371 B2
(45) Date of Patent: Sep. 15, 2020

(54) LASER LINE ILLUMINATOR FOR HIGH THROUGHPUT SEQUENCING

(71) Applicant: Illumina, Inc., San Diego, CA (US)

(72) Inventors: Yinghua Sun, San Diego, CA (US); Stanley S. Hong, San Diego, CA (US); Marco A. Krumbuegel, San Diego, CA (US); Peter Clarke Newman, San Diego, CA (US); Simon Prince, San Diego, CA (US); Dakota Watson, San Diego, CA (US); Wenyi Feng, San Diego, CA (US); Andrew James Carson, San Diego, CA (US); Frederick Erie, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 193 days.

(21) Appl. No.: 15/913,420

(22) Filed: Mar. 6, 2018

(65) Prior Publication Data
US 2018/0258468 A1 Sep. 13, 2018

Related U.S. Application Data

(60) Provisional application No. 62/468,883, filed on Mar. 8, 2017.

(30) Foreign Application Priority Data

May 5, 2017 (NL) ...................................... 2018855

(51) Int. Cl.
*C12Q 1/6809* (2018.01)
*G01N 21/39* (2006.01)
(Continued)

(52) U.S. Cl.
CPC ............ *C12Q 1/6809* (2013.01); *F21V 13/02* (2013.01); *F21V 19/02* (2013.01); *F21V 31/04* (2013.01);
(Continued)

(58) Field of Classification Search
CPC .......... F21V 31/04; F21V 19/02; F21V 13/02; G01N 21/39; G01N 21/6456;
(Continued)

(56) References Cited

U.S. PATENT DOCUMENTS 5,736,410 A * 4/1998 Zarling .................. B82Y 15/00
250/458.1
6,361,495 B1 * 3/2002 Grolman ................ A61B 3/165
600/401
(Continued)

FOREIGN PATENT DOCUMENTS

CN 102084003 6/2011
CN 101910399 11/2015
(Continued)

OTHER PUBLICATIONS

NL Application No. NL2018855 Search Report and Written Opinion dated Jan. 26, 2018, 12 pages.

*Primary Examiner* — Sang H Nguyen
(74) *Attorney, Agent, or Firm* — Illumina, Inc.

(57) ABSTRACT

Imaging systems including an objective lens and a line generation module are described herein. The objective lens may focus a first light beam emitted by the line generation module and a second light beam emitted by the line generation module at a focal point external to a sample so as to adjust line width. Line width may be increased to lower overall power density of a light beam on a surface of the sample such that the power density of the light beam on the surface of the sample is below a photosaturation threshold of a dye on the sample.

20 Claims, 16 Drawing Sheets

(51) Int. Cl.
  *F21V 13/02* (2006.01)
  *F21V 31/04* (2006.01)
  *F21V 19/02* (2006.01)
  *G02B 21/06* (2006.01)
  *G02B 27/09* (2006.01)
  *G01N 21/64* (2006.01)
  *G01N 21/03* (2006.01)

(52) U.S. Cl.
  CPC .............. *G01N 21/39* (2013.01); *G02B 21/06* (2013.01); *G02B 27/0927* (2013.01); *G01N 21/0332* (2013.01); *G01N 21/6456* (2013.01); *G01N 2021/392* (2013.01); *G01N 2021/6419* (2013.01); *G01N 2021/6478* (2013.01)

(58) Field of Classification Search
  CPC ....... G01N 21/0332; G01N 2021/6478; G01N 2021/6419; G01N 2021/392; G02B 21/06; G02B 27/0927; C12Q 1/6809
  See application file for complete search history.

(56) References Cited

U.S. PATENT DOCUMENTS

| | | | | |
|---|---|---|---|---|
| 7,441,703 | B2 * | 10/2008 | Moon | .................. G06K 7/1094 235/435 |
| 2003/0231408 | A1 | 12/2003 | Wolleschensky | |
| 2007/0081241 | A1 * | 4/2007 | Hayashi | ............. G02B 21/0024 359/443 |
| 2008/0117518 | A1 | 5/2008 | Wang | |
| 2009/0155793 | A1 | 6/2009 | Oliphant | |
| 2009/0250615 | A1 | 10/2009 | Oldham | |
| 2010/0157086 | A1 * | 6/2010 | Segale | ............... G01N 21/6458 348/222.1 |
| 2010/0238442 | A1 | 9/2010 | Heng | |
| 2011/0220775 | A1 * | 9/2011 | Triener | ............... G01N 21/6428 250/201.1 |
| 2014/0204389 | A1 * | 7/2014 | Mukoh | ............. G01B 9/02091 356/479 |
| 2016/0000535 | A1 * | 1/2016 | Atiya | .................... A61C 9/0046 433/29 |
| 2016/0334618 | A1 * | 11/2016 | Hargis | ............... G02B 26/0875 |
| 2018/0284411 | A1 * | 10/2018 | Dohi | .................. G02B 21/0048 |

FOREIGN PATENT DOCUMENTS

| | | |
|---|---|---|
| JP | 2004021259 | 1/2004 |
| JP | 2011-513734 | 4/2011 |
| JP | 2012-505431 | 3/2012 |
| JP | 2014-526686 | 10/2014 |
| TW | 201629456 | 8/2016 |
| WO | 2009/108795 | 9/2009 |
| WO | 2010/042576 | 4/2010 |
| WO | 2013/036927 | 3/2013 |
| WO | 2014005185 | 1/2014 |
| WO | 2016/043212 | 3/2016 |

* cited by examiner

PL : Powell Lens
M : Mirror
S : Shutter
DM: Dichroic Mirror
AP: Attenuator or Polarizer
FC: Flow Cell

LASER LINE ILLUMINATOR FOR HIGH THROUGHPUT SEQUENCING

CROSS REFERENCE TO RELATED APPLICATIONS

The present application claims the benefit of U.S. Provisional Patent Application No. 62/468,883 filed on Mar. 8, 2017 and titled "Laser Line Illuminator For High Throughput Sequencing," which is incorporated herein by reference in its entirety. The present application also claims the benefit of Netherlands Patent Application No. N2018855 filed on May 5, 2017, and titled "Laser Line Illuminator For High Throughput Sequencing."

BACKGROUND

Biological optical analysis instruments, such as genetic sequencers, tend to include multiple configurable components, each with multiple degrees of freedom. Increasing complexity of these biological optical analysis instruments has led to increased manufacturing and operation expense. Generally, these types of instruments benefit from precise alignment of their many internal optical components. In some genetic sequencing instruments, for example, internal components are generally aligned within precise tolerances. Many manufacturing techniques for such instruments involve installing all of the components on a precision plate, and then configuring and aligning each component. Component alignment may change during shipping or use. For example, temperature changes may alter alignments. Re-aligning each component takes time and skill. In some examples, there may be over 30 total degrees of freedom available across all of the components and they interact to each other. The large number of degrees of freedom complicates alignment and configuration and adds time and expense to system operation. Optical sequencer fabrication and operation may be simplified by reducing the degrees of freedom available across all system components through a modular architecture.

Optical sequencers may use laser line illumination to detect and sequence a biological specimen. For example, laser line illumination may enable high throughput scanning using a time delay integration (TDI) sensor to detect fluorescence emissions from a sample flowcell. The detected emissions may be used to identify and sequence genetic components of the biological sample. However, at high scanning speeds and/or laser output powers, functionality may be impacted by photo-saturation of the fluorophores and/or photo-bleaching of the fluorophores, and/or photo-induced damage to the sample. High power lasers can also cause damage to the objective lens, including the bonding adhesive, coatings and glass.

SUMMARY

Various implementations of the technologies disclosed herein describe imaging systems including an objective lens and a line generation module, where the imaging system is configured to adjust the width of lines emitted by the line generation module on a surface of a biological sample.

In one example, an imaging system includes: a line generation module and an objective lens. The line generation module includes a first light source to emit a first light beam at a first wavelength; a second light source to emit a second light beam at a second wavelength; and one or more line forming optics to shape a light beam emitted by the first light source into a line and a light beam emitted by the second light source into a line. In this example, the objective is configured to focus the first light beam and the second light beam at a focal point external to a sample of a sampling structure.

In one example, the sampling structure includes: a cover plate a substrate, and a liquid passage between the cover plate and substrate. In this example, the liquid passage includes a top interior surface and a bottom interior surface, and the sample is located at the top interior surface or at the bottom interior surface of the liquid passage. The focal point may be below the bottom interior surface of the liquid passage as to increase a line width of the first light beam and a line width of the second line beam at the top interior surface of the sampling structure. Alternatively, the focal point may be above the bottom interior surface of the liquid passage as to increase a line width of the first light beam and a line width of the second line beam at the top interior surface of the sampling structure.

In some implementations, the sampling structure is detachably coupled to the imaging system. In a particular implementation, the sampling structure is a flowcell.

In particular implementations, the focal point is between about 50 μm and about 150 μm below the bottom interior surface of the sampling structure. Alternatively, the focal point is between about 50 μm and about 150 μm above the bottom interior surface of the sampling structure.

In one implementation the imaging system includes a time delay integration (TDI) sensor to detect fluorescence emissions from the sample. In particular implementations, the TDI sensor has a pixel size between about 5 μm and about 15 μm, a sensor width between about 0.4 mm and about 0.8 mm, and a sensor length between about 16 mm and about 48 mm.

In one implementation, the line width of the first light beam and the line width of the second light beam is between about 10 μm and about 30 μm. In another implementation, the line length of the first light beam and the line length of the second light is between about 1 mm and about 1.5 mm.

In one implementation, the one or more line widening optics include a defocus lens, a prism, or a diffuser. In a particular implementation, the one or more line widening optics include a Powell lens positioned after a defocus lens in an optical path from the light sources to the objective lens.

In some implementations, the line width of the first light beam is increased to lower overall power density of the first light beam on a surface of the sample such that the power density of the first light beam on the surface of the sample is below a photosaturation threshold of a first dye on the sample, and the line width of the second light beam is increased to lower overall power density of the second light beam on a surface of the sample such that the power density of the second light beam on the surface of the sample is below a photosaturation threshold of a second dye on the sample.

In some implementations, the imaging system includes a z-stage for articulating the objective to adjust the line width of the first light beam and to adjust the line width of the second light beam. In further implementations, the imaging system includes a processor; and a non-transitory computer readable medium with computer executable instructions embedded thereon, the computer executable instructions configured to cause the system to: determine a quality of a signal from the TDI sensor; and articulate the objective in the z-axis to adjust the focal point and optimize the quality of the signal from the TDI sensor.

In another example, a DNA sequencing system includes: a line generation module and an objective lens. In this example, the line generation module may include: a plurality of light sources, each light source being to emit a light beam; and one or more line forming optics to shape each light beam into a line; and the objective lens or the one or more line forming optics are to increase a width of each line at a first surface or a second surface of a flowcell.

In implementations of this example, the objective lens is to focus each light beam at a focal point external to an interior surface of the flowcell as to increase the width of each line at the first surface or the second surface of the flowcell. The focal point may be between about 50 μm and about 150 μm below the bottom interior surface of the flowcell or between about 50 μm and about 150 μm above the top interior surface of the flowcell.

In some implementations, an objective lens of the imaging system is designed to be slightly finite conjugate to focus collimated laser light a distance between about 50 and about 150 um below the imaged surface.

In some implementations, the line generation module (LGM) provides uniform line illumination at a desired aspect ratio using a Powell lens, or other beam shaping optics. The system may be configured to optically adjust the diffractive limited focal point on objective plane (e.g., the flowcell surfaces. By adjusting the focal point above or below the surfaces of the flowcell, the beam width incident on the surfaces of the flowcell may be increased, and the laser power intensity at the sample and the flowcell may be decreased. The power density may be controlled below or near photosaturation of fluorophores for genetic sample detection (e.g., DNA, RNA, or other sample detection), while still satisfying TDI sensor integration tolerances on noise and speed. In some implementations, grouping components of a modular optical analytic system into modular sub-assemblies, and then installing the modular sub-assemblies on a precision plate or other stable structure may reduce relative degrees of freedom and simplify overall system maintenance.

For example, in one implementation, a modular optical analytic system may include sets of components grouped into four modular subassemblies. A first modular subassembly may include a plurality of lasers and corresponding laser optics grouped together into an LGM. A second modular subassembly may include lenses, tuning and filtering optics grouped into an emission optics module (EOM). A third modular subassembly may include camera sensors and corresponding optomechanics grouped into a camera module (CAM). A fourth modular subassembly may include focus tracking sensors and optics grouped into a focus tracking module (FTM). In some implementations, components of the system may group into different modular subassemblies. Components may be grouped into fewer or greater numbers of subassemblies depending on the specific application and design choices. Each modular subassembly may be pre-fabricated by incorporating the individual components onto a mounting plate or enclosure and precisely aligning and configuring the components within the modular sub-assembly to predetermined tolerances. Each modular sub-assembly may be fabricated to minimize degrees of freedom, such that only key components may be moved in one or more directions, or rotated, to enable precision alignment.

In some implementations, the LGM may be preconfigured on an LGM assembly bench designed with a precision interface and optics. The LGM assembly bench may include an assembly objective lens, a beam profiler, alignment targets, attenuator, precision plate, and translation stages. The assembly objective lens may have a field of view, focal length, and work distance that are greater than that of the EOM on the modular optics system, as to enable initial alignment of the laser modules and internal optics of the LGM. The beam profiler may be a 2D imaging sensor configured to detect and report beam intensity at various target locations. Alignment of the beams may include optimizing the beam position, intensity, pointing direction at these target locations by manipulating various internal optics and/or mirrors within the LGM. The manipulation of the various internal optical components and the evaluation of the laser using the beam profiler, may be an automated process or a manual process.

The system may also include a precision mounting plate. The precision mounting plate may be fabricated with alignment surfaces, such as mounting pins, grooves, slots, grommets, tabs, magnets, datum surfaces, tooling balls, or other surfaces designed to accept and mount each pre-fabricated and tested modular subassembly in its desired position. The precision mounting plate may include flat structures, non-flat structures, solid structures, hollow structures, honeycombed or latticed structures, or other types of rigid mounting structures as known in the art. In some examples, the precision mounting plate incorporates or is coupled to a stage motion assembly configured to maintain a level mounting surface and dampen vibration. The stage assembly may include actuators to control one or more control surfaces of an optical target to provide feedback to align the modular subassemblies (e.g., the EOM and CAM), for example, to reposition one or more optical components or sensors within predetermined tolerances. These precision motion devices may accurately position the illumination lines within the field of view of the optical imaging system, in stepwise or continuous motions.

Assembling a modular optical analytic system may include mounting each modular sub-assembly on the precision mounting plate and performing a final alignment using one or more control adjustments. In some examples, an optical analytic system with more than 30 degrees of freedom across each of its components may be reduced to a modular optical analytic system with fewer than 10 degrees of freedom across each of its components, wherein the components are grouped into pre-configured modular sub-assemblies. These remaining degrees of freedom may be selected to optimize inter-component alignment tolerances without implementing active or frequent alignment processes. In some implementations, one or more control adjustments within one or more modular subassemblies may be actuated using one or more corresponding actuators mounted in the subassemblies.

Sensors and/or detectors within one or more of the modular subassemblies (e.g., the CAM or the FTM) may be configured to transmit data to a computer, the computer including a processor and non-transitory computer readable media with machine-readable instructions stored thereon. The software may be configured to monitor optimal system performance, for example, by detecting and analyzing beam focus, intensity, and shape. In some examples, the system may include an optical target configured to display patterns specific to the alignment and performance of each modular subassembly. The software may then indicate via a graphical user interface when a particular modular subassembly is operating sub-optimally and recommend an open loop adjustment or implement a course of closed loop action to rectify the issue. For example, the software may be configured to transmit signals to the actuators to reposition specific components within predetermined tolerances, or may simply recommend swapping out the under-performing modular sub-assembly. The software may be operated locally or remotely via a network interface, enabling remoted system diagnostics and tuning.

Other features and aspects of the disclosed technology will become apparent from the following detailed description, taken in conjunction with the accompanying drawings, which illustrate, by way of example, the features in accordance with examples of the disclosed technology. The summary is not intended to limit the scope of any inventions described herein, which are defined by the claims and equivalents.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The technology disclosed herein, in accordance with one or more implementations, is described in detail with reference to the following figures. These figures are provided to facilitate the reader's understanding of the disclosed technology, and are not intended to be exhaustive or to limit the disclosure to the precise forms disclosed. Indeed, the drawings in the figures are provided for purposes of illustration only, and merely depict typical or example implementations of the disclosed technology. Furthermore, it should be noted that for clarity and ease of illustration, the elements in the figures have not necessarily been drawn to scale.

Figure 1A:
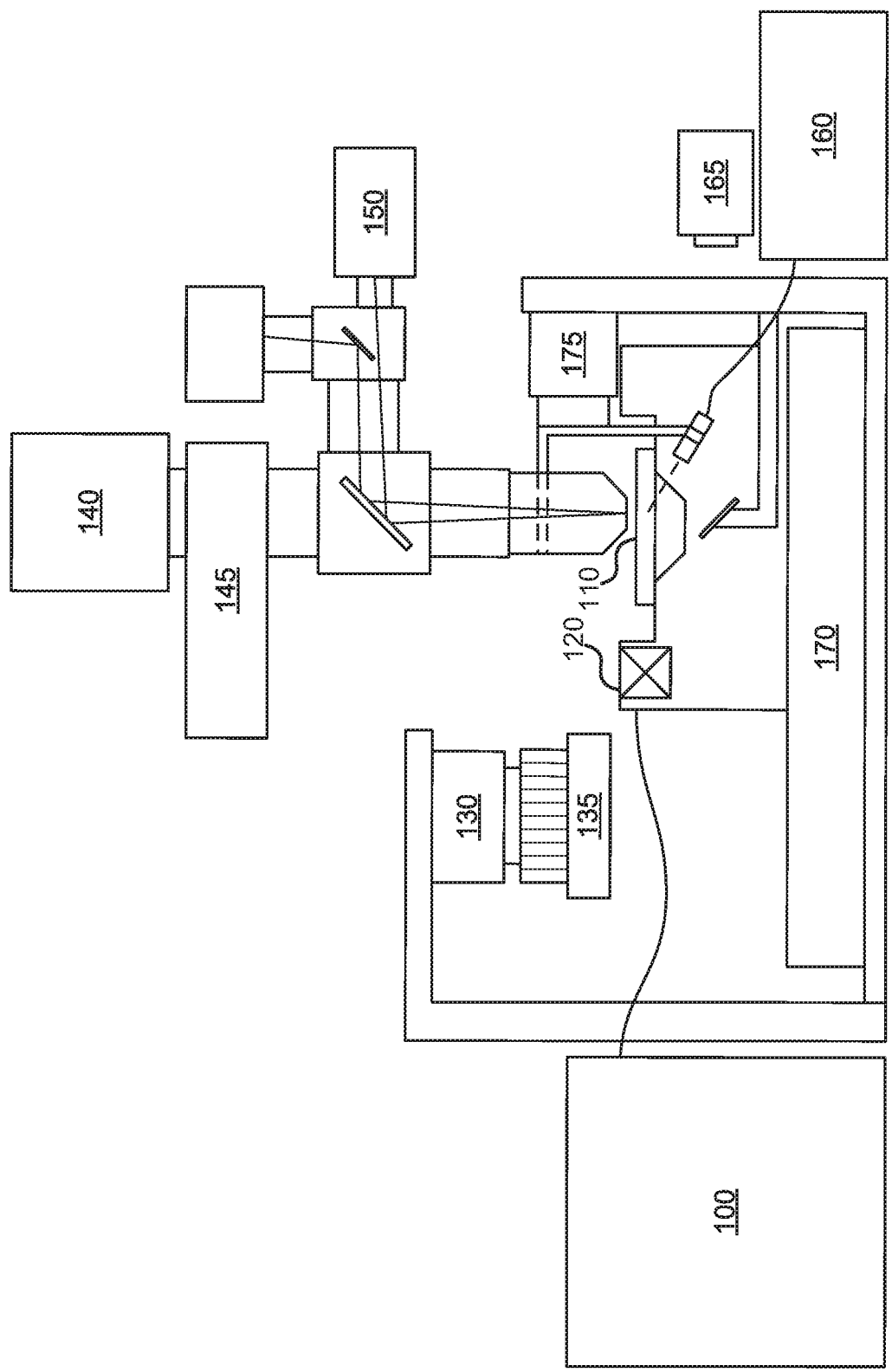
FIG. 1A illustrates a generalized block diagram of an example image scanning system with which systems and methods disclosed herein may be implemented.

It should be understood that the disclosed technology can be practiced with modification and alteration, and that the disclosed technology be limited only by the claims and the equivalents thereof.

DETAILED DESCRIPTION

As used herein, the term "xy plane" is intended to mean a 2 dimensional area defined by straight line axes x and y (according to the Cartesian coordinate system). When used in reference to a detector and an object observed by the detector, the area can be further specified as being orthogonal to the direction of observation between the detector and object being detected. When used herein to refer to a line scanner, the term "y direction" refers to the direction of scanning.

As used herein, the term "z direction" or "z axis" is intended to specify a direction or axis that is orthogonal to an area of an object that is observed by a detector. For example, the direction of focus for an optical system may be specified along the z axis.

Some implementations disclosed herein provide a modular optical system, such as ones that may be used for analyzing biological samples. Other implementations disclosed herein provide methods for assembling and installing modular optical systems for analyzing biological samples. One such optical system may be, or may be part of a genomic sequencing instrument. The instrument may be used to sequence DNA, RNA, or other biological samples.

Some genomic sequencing instruments operate by focusing coherent or incoherent light sources operating at different wavelengths through internal optics and onto the sample. Base pairs present in the sample then fluoresce and return light through the optics of the sequencer and onto an optical sensor, which can then detect the types of base pairs present. These types of instruments rely on precise alignment and tuning of the internal optics and are sensitive to drifting or misalignment of components caused by thermal effects (e.g., by heat from the light sources and electronics), as well as mechanical effects such as vibrations or incidental contact from users. Implementations of the present disclosure address these problems, and the installation and maintenance costs associated therewith, through a modular approach. Groupings of functionally related optical components may be pre-packaged, tested, and aligned as modular subassemblies. Each modular subassembly then may be treated as a field replaceable unit (FRU) which may be installed and aligned to the other modular subassemblies in the system by mounting the subassembly to a precision alignment plate.

Some implementations of the disclosure provide a system including a plurality of modular subassemblies and a precision mounting plate or, wherein each modular subassembly includes an enclosure and a plurality of optical components aligned to the enclosure. The enclosure may include a plurality of precision mounting structures, and each modular subassembly may be mechanically coupled to the precision mounting plate, such that each precision mounting structure from a modular subassembly attaches directly to a corresponding precision mounting structure located on the precision mounting plate or an adjacent modular subassembly. In some examples, the line generation module includes a first light source operating at a first wavelength, a second light source operating at a second wavelength, and a beam shaping lens aligned at a predetermined angle to each light source. For example, the first wavelength may be a green wavelength and the second wavelength may be a red wavelength. The beam shaping lens may be a Powell lens.

In some implementations, the emissions optics module may include an objective lens that is optically coupled to a light generation module, and a tube lens that is optically coupled to the objective lens. The objective lens focuses light onto a flowcell positioned at a predetermined distance from the flowcell. The objective may articulate along a longitudinal axis, and the tube lens may include a lens component that also articulates along a longitudinal axis within the tube lens to ensure accurate imaging. For example, the lens component may move to compensate for spherical aberration caused by articulation of the objective to image one or more surfaces of the flowcell.

In some examples, the flowcell may include a translucent cover plate, a substrate, and a liquid sandwiched therebetween, and a biological sample may be located at an inside surface of the translucent cover plate or an inside surface of the substrate. For example, the biological sample may include DNA, RNA, or another genomic material which may be sequenced.

The focus tracking module may include a focus tracking light source and a focus tracking sensor, wherein the light source may generate a light beam, transmit the light beam through the plurality of optical components such that the light beam terminates at the focus tracking sensor. The focus tracking sensor may be communicatively coupled to a processor and a non-transitory computer readable medium with machine-readable instructions stored thereon. The machine-readable instructions, when executed, may cause the processor to receive an output signal from the focus tracking sensor and analyze the output signal to determine a set of characteristics of the light beam. In some examples, the machine-readable instructions, when executed, further cause the processor to generate a feedback signal indicating that one or more of the optical components should be reconfigured to optimize the set of characteristics of the light beam. One or more of the modular subassemblies may be a field replaceable unit. The precision mounting structures may include a slot, a datum, a tab, a pin, or a recessed cavity, other mechanical mounting structures as known in the art, or any combination thereof.

In some examples, the camera module includes a plurality of optical sensors, and the light generation module includes a plurality of light sources, wherein each optical sensor may be oriented to receive and detect a light beam from corresponding light source.

Before describing various implementations of the systems and methods disclosed herein, it is useful to describe an example environment with which the systems and methods can be implemented. One such example environment is that of an optical system, such as that illustrated in FIG. 1A. The example optical system may include a device for obtaining or producing an image of a region. The example outlined in FIG. 1 shows an example imaging configuration of a backlight design implementation.

As can be seen in the example of FIG. 1A, subject samples are located on sample structure or container 110 (e.g., a flowcell as disclosed herein), which is positioned on a sample stage 170 under an objective lens. Light source 160 and associated optics direct a beam of light, such as laser light, to a chosen sample location on the sample container 110. The sample fluoresces and the resultant light is collected by the objective lens and directed to a photo detector 140 to detect the florescence. Sample stage 170 is moved relative to objective lens to position the next sample location on sample container 110 at the focal point of the objective lens. Movement of sample stage 170 relative to objective lens can be achieved by moving the sample stage itself, the objective lens, the entire optical stage, or any combination of the foregoing. Further implementations may also include moving the entire imaging system over a stationary sample.

Fluid delivery module or device 100 directs the flow of reagents (e.g., fluorescent nucleotides, buffers, enzymes, cleavage reagents, etc.) to (and through) sample container 110 and waste valve 120. In particular implementations, the sample container 110 can be implemented as a flowcell that includes clusters of nucleic acid sequences at a plurality of sample locations on the sample container 110. The samples to be sequenced may be attached to the substrate of the flowcell, along with other optional components.

The system also comprises temperature station actuator 130 and heater/cooler 135 that can optionally regulate the temperature of conditions of the fluids within the sample container 110. Camera system 140 can be included to monitor and track the sequencing of sample container 110. Camera system 140 can be implemented, for example, as a CCD camera, which can interact with various filters within filter switching assembly 145, objective lens, and focusing laser/focusing laser assembly 150. Camera system 140 is not limited to a CCD camera and other cameras and image sensor technologies can be used.

Light source 160 (e.g., an excitation laser within an assembly optionally comprising multiple lasers) or other light source can be included to illuminate fluorescent sequencing reactions within the samples via illumination through fiber optic interface (which can optionally comprise one or more re-imaging lenses, a fiber optic mounting, etc). Low watt lamp 165, focusing laser 150, and reverse dichroic are also presented in the example shown. In some implementations focusing laser 150 may be turned off during imaging. In other implementations, an alternative focus configuration can include a second focusing camera (not shown), which can be a quadrant detector, a Position Sensitive Detector (PSD), or similar detector to measure the location of the scattered beam reflected from the surface concurrent with data collection.

Although illustrated as a backlit device, other examples may include a light from a laser or other light source that is directed through the objective lens onto the samples on sample container 110. Sample container 110 can be ultimately mounted on a sample stage 170 to provide movement and alignment of the sample container 110 relative to the objective lens. The sample stage can have one or more actuators to allow it to move in any of three dimensions. For example, in terms of the Cartesian coordinate system, actuators can be provided to allow the stage to move in the X, Y and Z directions relative to the objective lens. This can allow one or more sample locations on sample container 110 to be positioned in optical alignment with objective lens.

A focus (z-axis) component 175 is shown in this example as being included to control positioning of the optical components relative to the sample container 110 in the focus direction (typically referred to as the z axis, or z direction). Focus component 175 can include one or more actuators physically coupled to the optical stage or the sample stage, or both, to move sample container 110 on sample stage 170 relative to the optical components (e.g., the objective lens) to provide proper focusing for the imaging operation. For example, the actuator may be physically coupled to the respective stage such as, for example, by mechanical, magnetic, fluidic or other attachment or contact directly or indirectly to or with the stage. The one or more actuators can be configured to move the stage in the z-direction while maintaining the sample stage in the same plane (e.g., maintaining a level or horizontal attitude, perpendicular to the optical axis). The one or more actuators can also be configured to tilt the stage. This can be done, for example, so that sample container 110 can be leveled dynamically to account for any slope in its surfaces.

Focusing of the system generally refers to aligning the focal plane of the objective lens with the sample to be imaged at the chosen sample location. However, focusing can also refer to adjustments to the system to obtain a desired characteristic for a representation of the sample such as, for example, a desired level of sharpness or contrast for an image of a test sample. Because the usable depth of field of the focal plane of the objective lens may be small (sometimes on the order of 1 μm or less), focus component 175 closely follows the surface being imaged. Because the sample container is not perfectly flat as fixtured in the instrument, focus component 175 may be set up to follow this profile while moving along in the scanning direction (herein referred to as the y-axis).

The light emanating from a test sample at a sample location being imaged can be directed to one or more detectors 140. Detectors can include, for example a CCD camera. An aperture can be included and positioned to allow only light emanating from the focus area to pass to the detector. The aperture can be included to improve image quality by filtering out components of the light that emanate from areas that are outside of the focus area. Emission filters can be included in filter switching assembly 145, which can be selected to record a determined emission wavelength and to cut out any stray laser light.

In various implementations, sample container 110 can include one or more substrates upon which the samples are provided. For example, in the case of a system to analyze a large number of different nucleic acid sequences, sample container 110 can include one or more substrates on which nucleic acids to be sequenced are bound, attached or associated. In various implementations, the substrate can include any inert substrate or matrix to which nucleic acids can be attached, such as for example glass surfaces, plastic surfaces, latex, dextran, polystyrene surfaces, polypropylene surfaces, polyacrylamide gels, gold surfaces, and silicon wafers. In some applications, the substrate is within a channel or other area at a plurality of locations formed in a matrix or array across the sample container 110.

Although not illustrated, a controller can be provided to control the operation of the scanning system. The controller can be implemented to control aspects of system operation such as, for example, focusing, stage movement, and imaging operations. In various implementations, the controller can be implemented using hardware, algorithms (e.g., machine executable instructions), or a combination of the foregoing. For example, in some implementations the controller can include one or more CPUs or processors with associated memory. As another example, the controller can comprise hardware or other circuitry to control the operation, such as a computer processor and a non-transitory computer readable medium with machine-readable instructions stored thereon. For example, this circuitry can include one or more of the following: field programmable gate array (FPGA), application specific integrated circuit (ASIC), programmable logic device (PLD), complex programmable logic device (CPLD), a programmable logic array (PLA), programmable array logic (PAL) or other similar processing device or circuitry. As yet another example, the controller can comprise a combination of this circuitry with one or more processors.

Although the systems and methods may be described herein from time to time in the context of this example system, this is only one example with which these systems and methods may be implemented. After reading this description, one of ordinary skill in the art will understand how the systems and methods described herein can be implemented with this and other scanners, microscopes and other imaging systems.

Figure 1B:
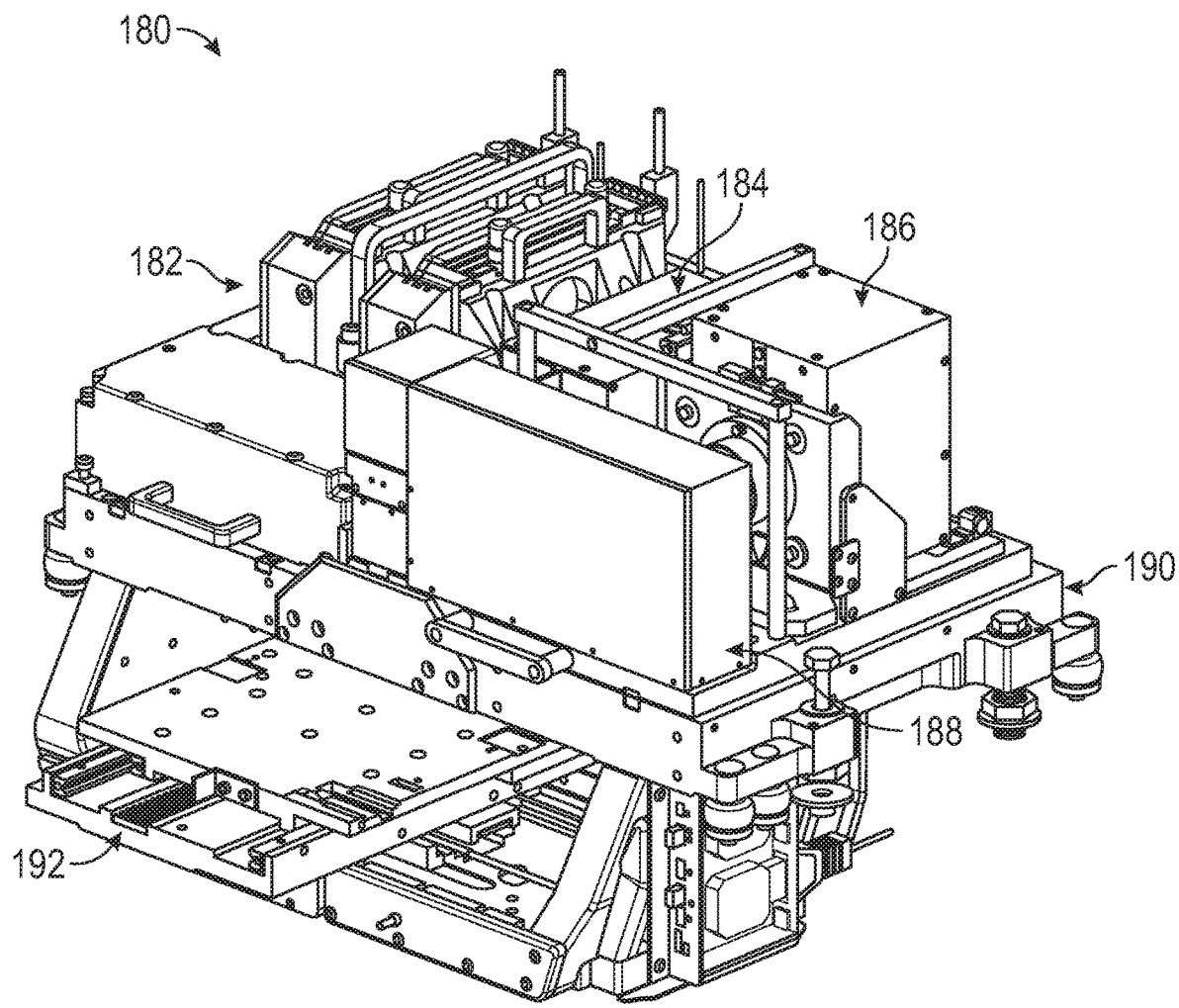
FIG. 1B is a perspective view diagram illustrating an example modular optical analytic system in accordance with implementations disclosed herein.

Implementations of the technology disclosed herein provide modular optical analytic systems and methods. FIG. 1B is a perspective view diagram illustrating an example modular optical analytic system 180. System 180 may include a plurality of modular subassemblies. For example, in some implementations, system 180 comprises four subassembly modules: line generation module (LGM) 182, focus tracking module (FTM) 184, camera module (CAM) 186, and emission optical module (EOM) 188. As used herein in the context of the LGM, FTM, EOM, or CAM, a module refers to a hardware unit (e.g., a modular subassembly).

In some implementations, LGM 182 may include one or more light sources. In some implementations, the one or more light sources may include coherent light sources, such as laser diodes. In some examples, LGM 182 may include a first light source configured to emit light in red wavelengths, and a second light source configured to emit light in green wavelengths. LGM 182 may further include optical components, such as focusing surfaces, lenses, reflective surfaces, or mirrors. The optical components may be positioned within an enclosure of LGM 182 as to direct and focus the light emitted from the one or more light sources into an adjacent modular subassembly. One or more of the optical components of LGM 182 may also be configured to shape the light emitted from the one or more light sources into desired patterns. For example, in some implementations, the optical components may shape the light into line patterns (e.g., by using one or more Powell lenses, or other beam shaping lenses, diffractive or scattering components). One or more of the optical components may be located in one or more of the other modular subassemblies. One or more of the modular subassemblies may also include one or more field replaceable sub-components. For example, LGM 182 may include one or more laser modules which may be individually removed from LGM 182 and replaced.

In some examples, the adjacent modular subassembly (coupled to LGM 182) may be EOM 188. Light from the one or more light sources of LGM 182 may be directed out of LGM 182 and into EOM 188 through an interface baffle attached to LGM 182 and/or EOM 188. For example, the interface baffle may be an aperture shaped to enable light to pass through its center, while obscuring interference from external light sources. EOM 188 may also include an objective, a tube lens, and or other optical components configured to shape, direct, and/or focus fluorescent light excited by the one or more light sources of LGM 182.

Light passing through EOM 188 may be directed into one of the other adjacent modular subassemblies, for example, CAM 186, through an interface port. CAM 186 may include one or more light sensors. In some implementations, a first light sensor may be configured to detect light from the first light source of LGM 182 (e.g., in a red wavelength), and a second light sensor may be configured to detect light from the second light source of LGM 182 (e.g., a green wavelength). The light sensors of CAM 186 may be positioned within an enclosure in a configuration such as to detect light from two incident light beams wherein the incident light beams may be spaced apart by a predetermined distance (e.g., between 1 mm and 10 mm) based on the pitch of the two sensors. In some examples, the first light sensor and the second light sensor may be spaced apart from each other by between 3 mm and 8 mm. The light sensors may have a detection surface sufficiently sized to allow for beam drift, for example, due to thermal effects or mechanical creep. Output data from the light sensors of CAM 186 may be communicated to a computer processor. The computer processor may then implement computer software program instructions to analyze the data and report or display the characteristics of the beam (e.g., focus, shape, intensity, power, brightness, position) to a graphical user interface (GUI), and/or automatically control actuators and laser output to optimize the laser beam. Beam shape and position may be optimized by actuating internal optics of system 180 (e.g., tilting mirrors, articulating lenses, etc.).

FTM 184 may also couple to EOM 188 through an interface port. FTM 184 may include instruments to detect and analyze the alignment and focus of all of the optical components in system 180. For example, FTM 184 may include a light source (e.g., a laser), optics, and a light sensor, such as a digital camera or CMOS chip. The laser may be configured to transmit light source and optics may be configured to direct light through optical components in system 180 and the light sensor may be configured to detect light being transmitted through optical components in system 180 and output data to a computer processor. The computer processor may then implement computer software program instructions to analyze the data and report or display the characteristics of the laser beam (e.g., focus, intensity, power, brightness, position) to a graphical user interface (GUI), and/or automatically control actuators and laser output to optimize the laser beam. In some examples, FTM 184 may include a cooling system, such as an air or liquid cooling system as known in the art.

In some implementations, LGM 182 may include light sources that operate at higher powers to also accommodate for faster scanning speeds (e.g., the lasers in LGM 182 may operate at a five times greater power output). Similarly, the light source of laser module may operate at a higher output power and/or may also include a high resolution optical sensor to achieve nanometer scale focus precision to accommodate for faster scanning speeds. The cooling system of FTM 184 may be enhanced to accommodate the additional heat output from the higher powered laser using cooling techniques known in the art.

In one example, each modular subassembly may mechanically couple to one or more other modular subassemblies, and/or to a precision mounting plate 190. In some implementations, precision mounting plate 190 may mechanically couple to a stage assembly 192. Stage assembly 192 may include motion dampers, actuators to actuate one or more components within one or more modular subassemblies, cooling systems, and/or other electronics or mechanical components as known in the art.

The modular subassemblies may be prefabricated, configured, and internally aligned. In some implementations, a control unit may be electronically coupled to stage assembly 192 and communicatively coupled to a user interface to enable automatic or remote manual alignment of one or more modular subassemblies after they have been coupled to precision mounting plate 190. Each modular subassembly may be a field replaceable unit (FRU), such that it may be removed from precision mounting plate 190 and replaced with another functionally equivalent modular subassembly without disturbing the alignment or configuration of the other modular subassemblies in the system.

Each module is pre-aligned and pre-qualified before integration into system 180. For example, assembly and configuration of LGM 182 may include the mechanical coupling of one or more lasers or laser diodes into an enclosure, and installation of control electronics to operate the lasers or laser diodes. The entire LGM 182 may then be mounted on a test bed and operated to align the laser diodes within the enclosure, as well as any optics or other components. The LGM enclosure may include external mounting structures, such as mounting pins, datum, notches, tabs, slots, ridges, or other protrusions or indentations configured to align the LGM 182 to the test bed, as well as to precision mounting plate 190 when installed in system 180. Once LGM 182 is configured and tested, it may be either installed in a system 180, or packaged and stored or shipped as a field replaceable unit (FRU).

Other modular subassemblies, such as FTM 184, CAM 186, or EOM 188, may be similarly assembled, configured, and tested prior to installation on system 180. Each modular subassembly may be assembled using mechanical coupling methods to limit mobility of internal components within the subassembly as desired. For example, components may be locked in place with fasteners or welds to stop mobility of once the component is aligned to the other components or the enclosure of the modular subassembly. Some components, as desired, may be coupled with articulating joints or allowed to move within an enclosure such that their relative orientation may be adjusted after installation on precision mounting plate 190. For example, each modular subassembly's relative positioning may be controlled precisely using predetermined mechanical tolerances (e.g., by aligning datum to receiving notches in an adjoining modular subassembly or in precision mounting plate 190) such as to enable overall optical alignment of system 180 with a limited number of adjustable degrees of freedom (e.g., fewer than 10 overall degrees of freedom in some implementations).

Figure 1C:
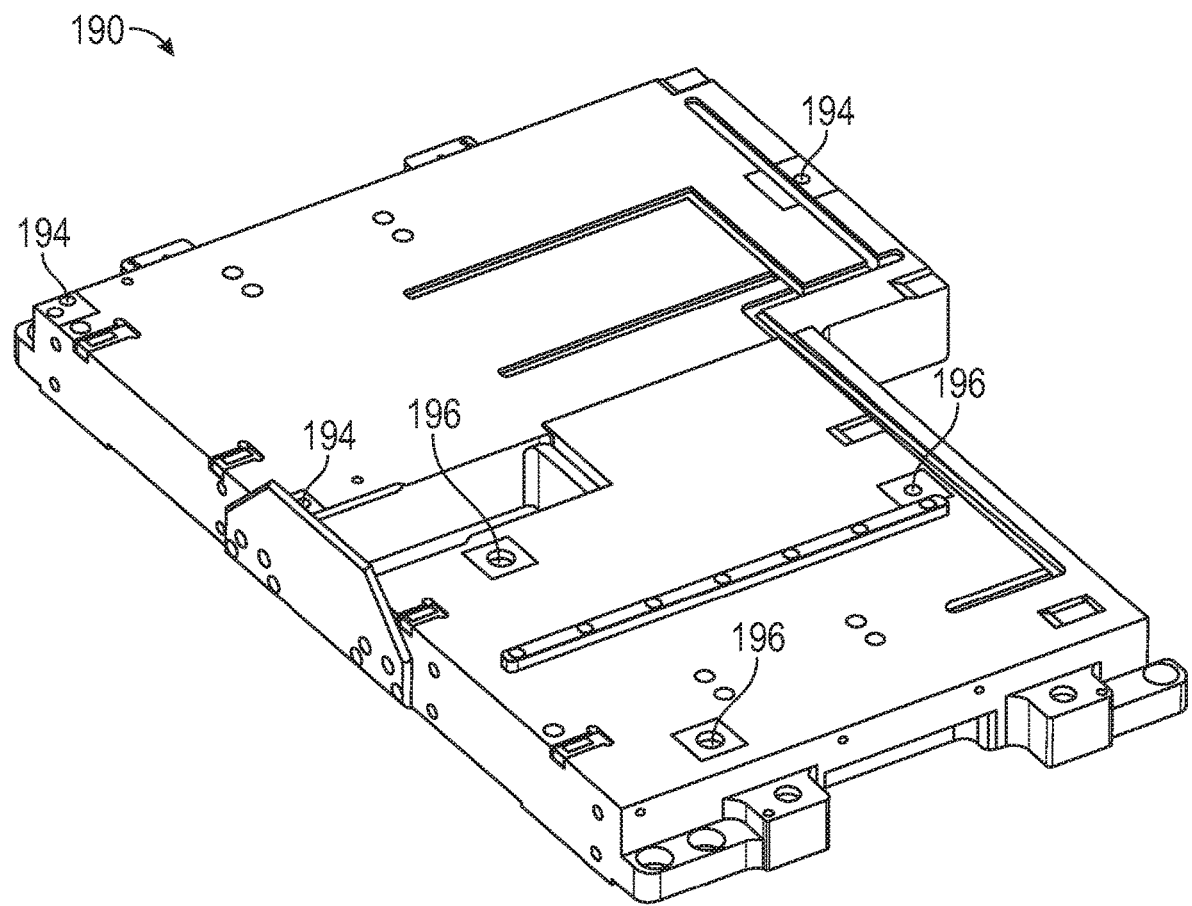
FIG. 1C is a perspective view diagram illustrating an example precision mounting plate in accordance with implementations disclosed herein.

FIG. 1C is a perspective view diagram illustrating an example precision mounting plate 190. Precision mounting plate 190 may be fabricated from light weight, rigid, and heat tolerant materials. In some implementations, precision mounting plate 190 may be fabricated from a metal (e.g., aluminum), ceramic, or other rigid materials as known in the art. Precision mounting plate 190 may include precision alignment structures configured to mechanically couple to corresponding precision alignment structures incorporated on the enclosures or housings of one or more of the modular subassemblies. For example, precision alignment structures may include mounting pins, datums, tabs, slots, notches, grommets, magnets, ridges, indents, and/or other precision mounting structures shaped to align a first surface (e.g., on precision mounting plate 190) to a second surface (e.g., an outer surface of the enclosure or housing of a modular subassembly. Referring to FIG. 1C, example precision mounting plate 190 may include a plurality of LGM precision mounting structures 194 configured to accept and mechanically couple to corresponding precision mounting structures located on an outer surface of the enclosure of LGM 182. Similarly, precision mounting plate 190 may include a plurality of EOM precision mounting structures 196 configured to accept and mechanically couple to corresponding precision mounting structures located on an outer surface of the enclosure of EOM 188. By locating LGM 182 and EOM 188 onto precision mounting plate 190 using the precision mounting structures, LGM 182 and EOM 188 will align to each other. Precision alignment structures located on the enclosures of other modular subassemblies (e.g., FTM 184 and CAM 186) may then mechanically couple to respective precision alignment structures located on the enclosures of either LGM 182 or EOM 188, or on precision mounting plate 190.

Figure 1D:
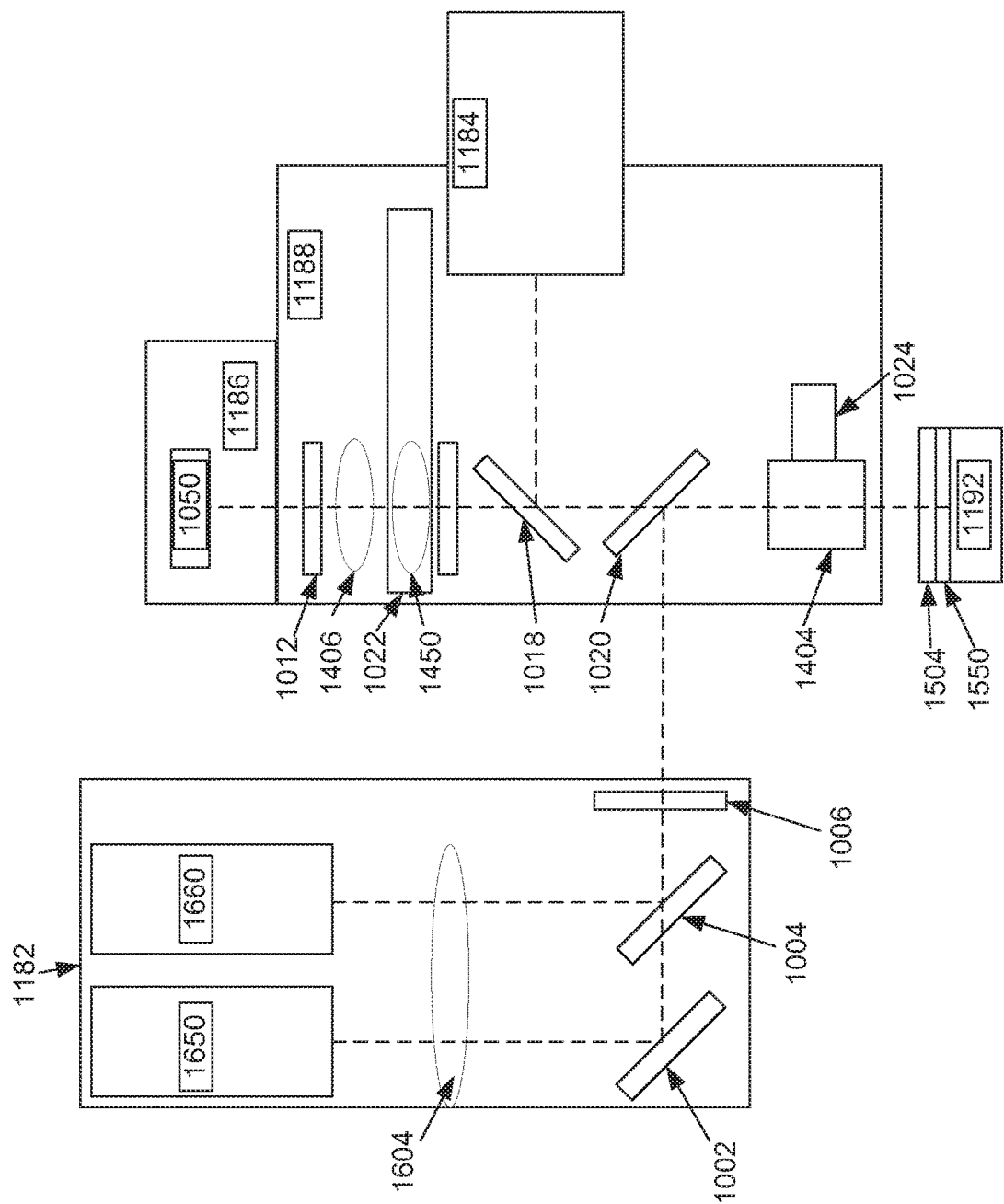
FIG. 1D illustrates a block diagram of an example modular optical analytic system consistent with implementations disclosed herein.
Figure 1E:
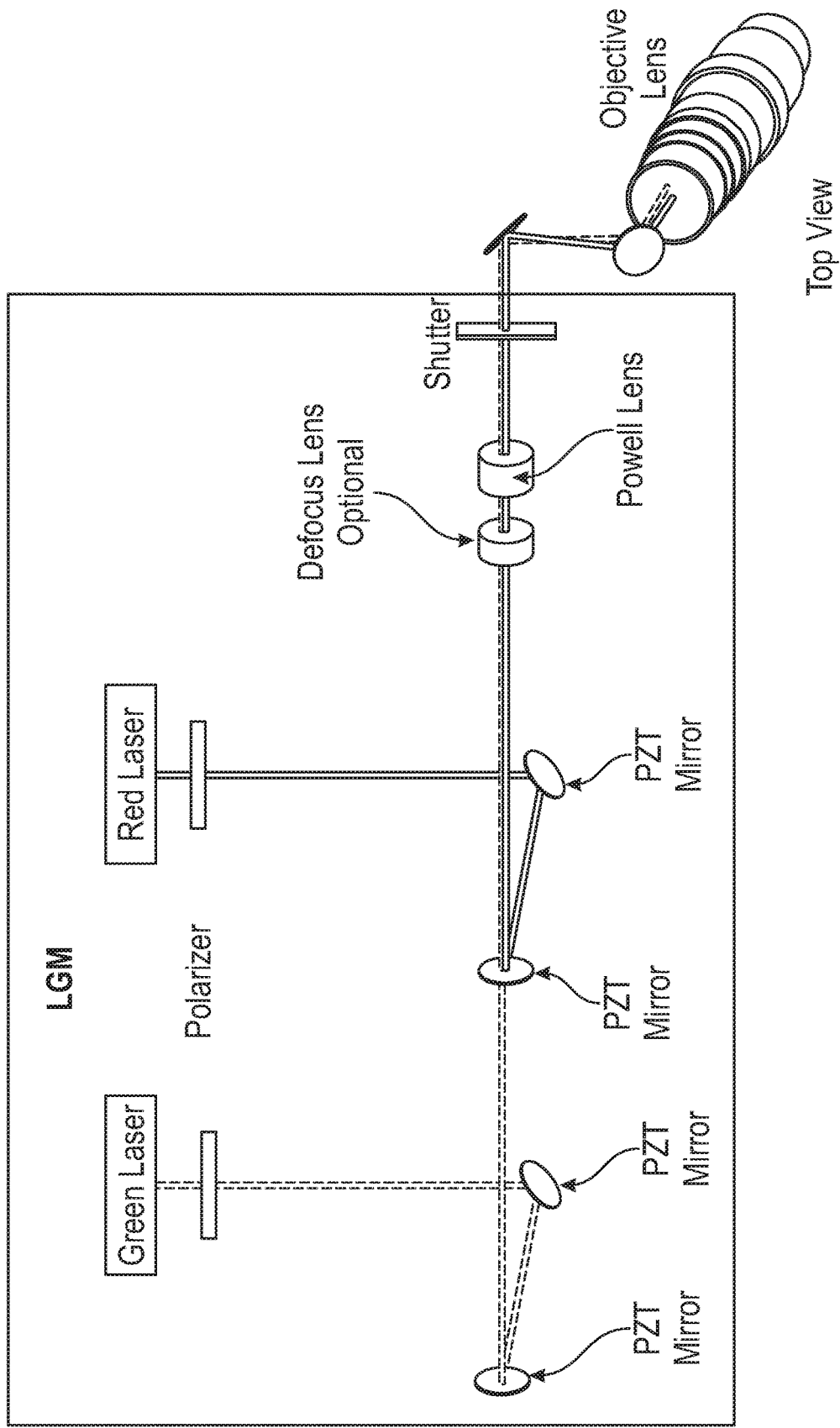
FIG. 1E illustrates a perspective view of an example modular optics analytic system, consistent with implementations disclosed herein.

FIG. 1D illustrates a block diagram of an example modular optical analytic system. In some implementations, a modular optical analytic system may include an LGM 1182 with two light sources, 1650 and 1660, disposed therein. Light sources 1650 and 1660 may be laser diodes, diode pumped solid state lasers, or other light sources as known in the art, which output laser beams at different wavelengths (e.g., red or green light). The light beams output from laser sources 1650 and 1660 may be directed through a beam shaping lens or lenses 1604. In some implementations, a single light shaping lens may be used to shape the light beams output from both light sources. In other implementations, a separate beam shaping lens may be used for each light beam. In some examples, the beam shaping lens is a Powell lens, such that the light beams are shaped into line patterns.

LGM 1182 may further include mirrors 1002 and 1004. A light beam generated by light source 1650 may reflect off 1002 as to be directed through an aperture or semi-reflective surface of mirror 1004, and into EOM 1188 through a single interface port. Similarly, a light beam generated by light source 1660 may reflect off of mirror 1003 and mirror 1004 as to be directed into EOM 1188 through a single interface port. In some examples, an additional set of articulating mirrors may be incorporated adjacent to mirror 1004 to provide additional tuning surfaces, for example, as illustrated in FIG. 1H.

Both light beams may be combined using dichroic mirror 1004. Both light beams may be directed through line forming optics, such as a Powell lens. Mirrors 1002 and 1004 may each be configured to articulate using manual or automated controls as to align the light beams from light sources 1650 and 1660. The light beams may pass through a shutter element 1006. EOM 1188 may include objective 1404 and a z-stage 1024 which moves objective 1404 longitudinally closer to or further away from a target 1192. For example, target 1192 may include a liquid layer 1550 and a translucent cover plate 1504, and a biological sample may be located at an inside surface of the translucent cover plate as well an inside surface of the substrate layer located below the liquid layer. The z-stage may then move the objective as to focus the light beams onto either inside surface of the flowcell (e.g., focused on the biological sample). The biological sample may be DNA, RNA, proteins, or other biological materials responsive to optical sequencing as known in the art. In some implementations, the objective may be configured to focus the light beams at a focal point beyond the flowcell, such as to increase the line width of the light beams at the surfaces of the flowcell.

EOM 1188 may also include semi-reflective mirror 1020 to direct light through objective 1404, while allowing light returned from target 1192 to pass through. In some implementations, EOM 1188 may include a tube lens 1406 and a corrective lens 1450. Corrective lens 1450 may be articulated longitudinally either closer to or further away from objective 1404 using a z-stage 1022 as to ensure accurate imaging, e.g., to correct spherical aberration caused by moving objective 1404, and/or from imaging through a thicker substrate. Light transmitted through corrective lens 1450 and tube lens 1406 may then pass through filter element 1012 and into CAM 1186. CAM 1186 may include one or more optical sensors 1050 to detect light emitted from the biological sample in response to the incident light beams.

In some examples, EOM 1188 may further include semi-reflective mirror 1018 to reflect a focus tracking light beam emitted from FTM 1184 onto target 1192, and then to reflect light returned from target 1192 back into FTM 1184. FTM 1184 may include a focus tracking optical sensor to detect characteristics of the returned focus tracking light beam and generate a feedback signal to optimize focus of objective 1404 on target 1192.

LGM 1182 is configured to generate a uniform line illumination through an objective lens. For example, the objective lens may be located on EOM 1188, or on an LGM alignment system used to align the internal components of the LGM when the LGM is being assembled or maintained (e.g., and is physically separated from the modular optical analytic system). The LGM may use one or more Powell lenses to spread and/or shape the laser beams from single or near-single mode laser light sources. Other beam shaping optics may be used to control uniformity and increase tolerance such as an active beam expander, an attenuator, one relay lenses, cylindrical lenses, actuated mirrors, diffractive elements, and scattering components. Laser beams may intersect at the back focal point of objective lens to provide better tolerance on flowcell surfaces (e.g., as illustrated in FIG. 1.1). A Powell lens may be located near the objective lens, or near a relay lens. The fan angle of the laser beam entering the imaging optics may be adjusted to match the field view of imaging optics.

The direction, size, and/or polarization of the laser beams may be adjusted by using lenses, mirrors, and/or polarizers. Optical lenses (e.g., cylindrical, spherical, or aspheric) may be used to actively adjust the illumination focus on dual surfaces of the flowcell target. The light modules on LGM 1182 may be replaceable individually for field service. LGM 1182 may include multiple units and each unit is designed for particular/different wavelengths and polarization. Stacking multiple units may be used to increase the laser power and wavelength options. Two or more laser wavelengths can be combined with dichroics and polarizers.

To avoid photo-bleaching on adjacent area or photo-saturation of fluorophores, illumination line profiles may be adjusted to fall within predetermined intensity ratio tolerances inside/outside imaging region. By widening the laser line patterns at the flowcell and/or sensor, higher scan speeds and laser powers may be employed (e.g., power and throughput may be increased more than four-fold without experiencing photo-saturation or photo-bleaching, or damaging the laser modules). In some examples, laser power densities of more than 20 $kW/cm^2$ at the flowcell may over-saturate the fluorophores in the flowcell. When this occurs, the emission signal detected at the sensor will not increase linearly with an increase in excitation power from the laser modules.

Methods for widening illumination lines using optics may include: adding a defocus lens, prism array, or diffuser after or before the Powell lens. In some implementations, these methods may also include reducing the laser illumination beam size and/or reducing objective lens infinite conjugation design. FIG. 1K illustrates a block diagram of an LGM and EOM system used to widen the laser line pattern on a flowcell to avoid photo-saturation and photo-bleaching. The laser beam line width incident on the flowcell may be increased to reduce excitation power density and avoid photo-saturation. Line width may be increased, for example, by incorporating a defocus lens, prism, array, or diffuser either in front of or behind the Powell lens. In some implementations, the line width may be increased by defocusing the objective lens, as illustrated in FIG. 1K (e.g., moving the objective lens in the Z-axis) to focus the line pattern beyond the surfaces of the flowcell. In some examples, defocusing the line pattern to a distance of between about 50 microns and about 150 microns from a distal surface of the flowcell may generate a line width larger than 10 microns, and effectively reduce photo-saturation and photo-bleaching effects.

When using a TDI sensor, the line width-to-beam intensity profile may be balanced with signal-to-noise tolerances of the TDI sensor. For example, at very wide line widths, the signal-to-noise ratio may be too low to be effective.

Figure 1F:
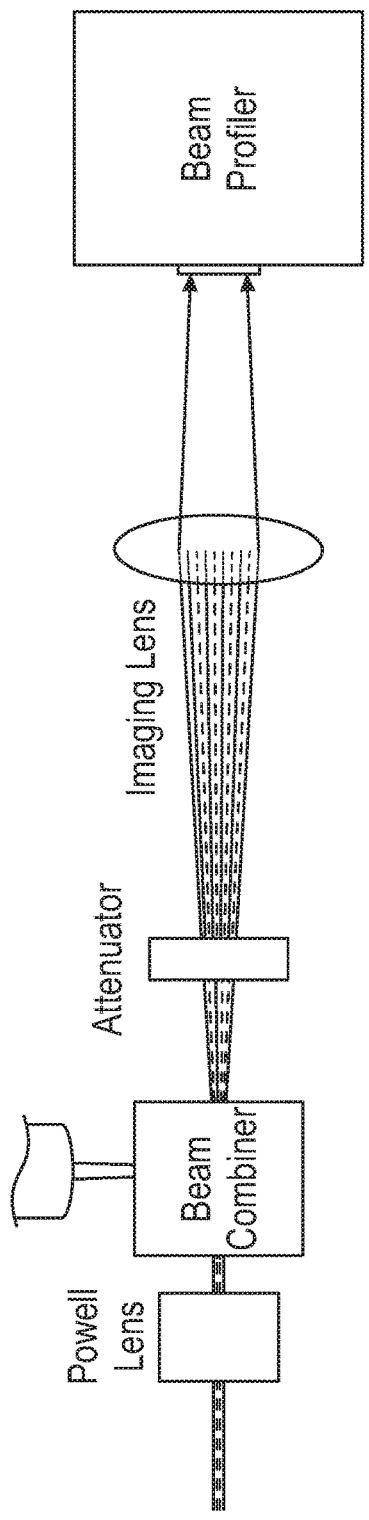
FIG. 1F illustrates a block diagram of a line generation module (LGM) alignment system, consistent with implementations disclosed herein.
Figure 1G:
FIG. 1G illustrates a perspective view of an LGM alignment system, consistent with implementations disclosed herein.
Figure 1G:
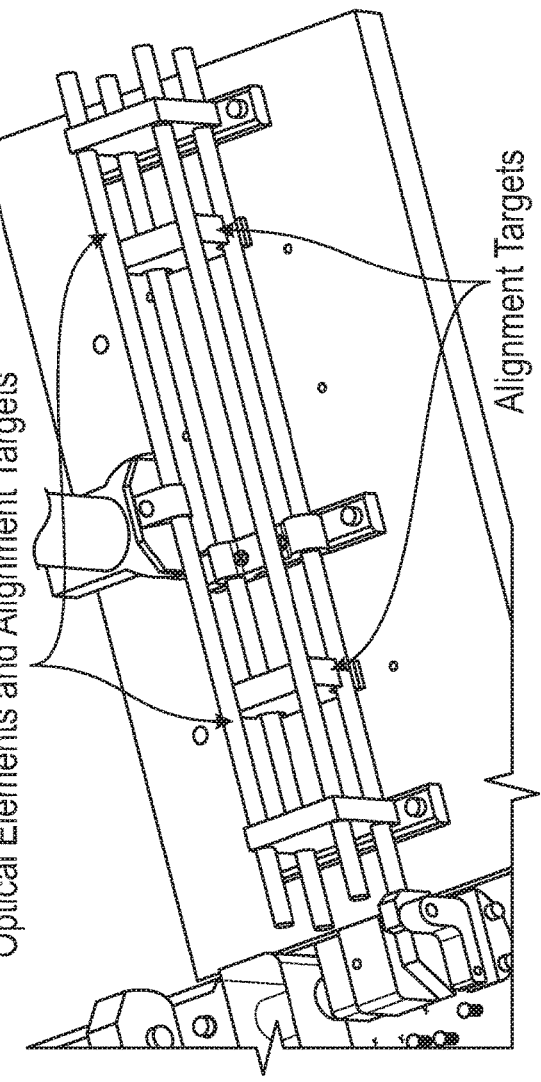
Figure 1I:
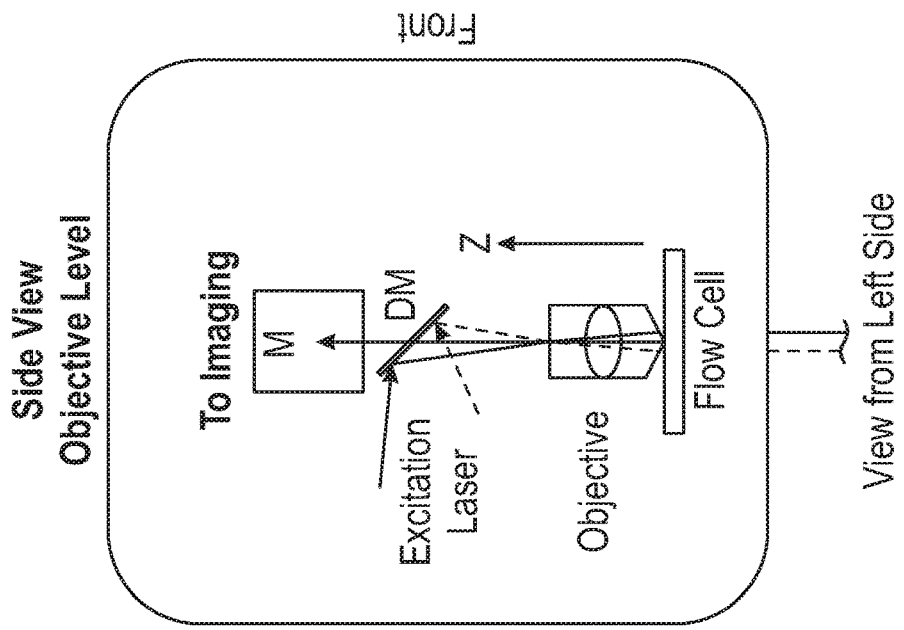
FIG. 1I illustrates a side view of an example modular optical analytic system consistent with implementations disclosed herein.
Figure 1H:
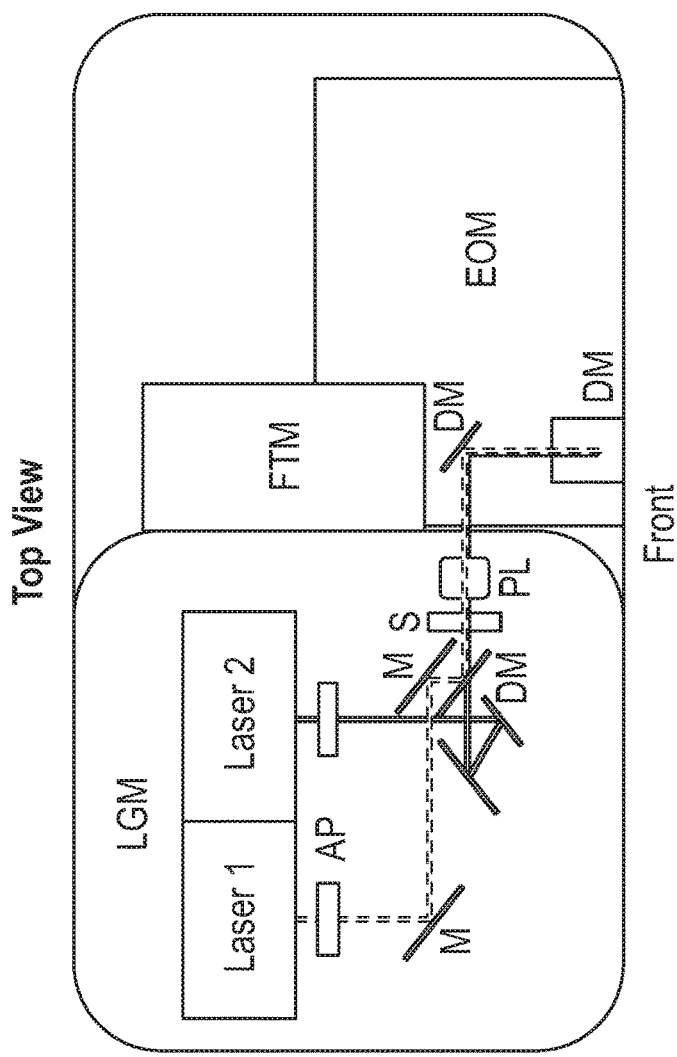
FIG. 1H illustrates a top down view of an example modular optical analytic system consistent with implementations disclosed herein.
Figure 1J:
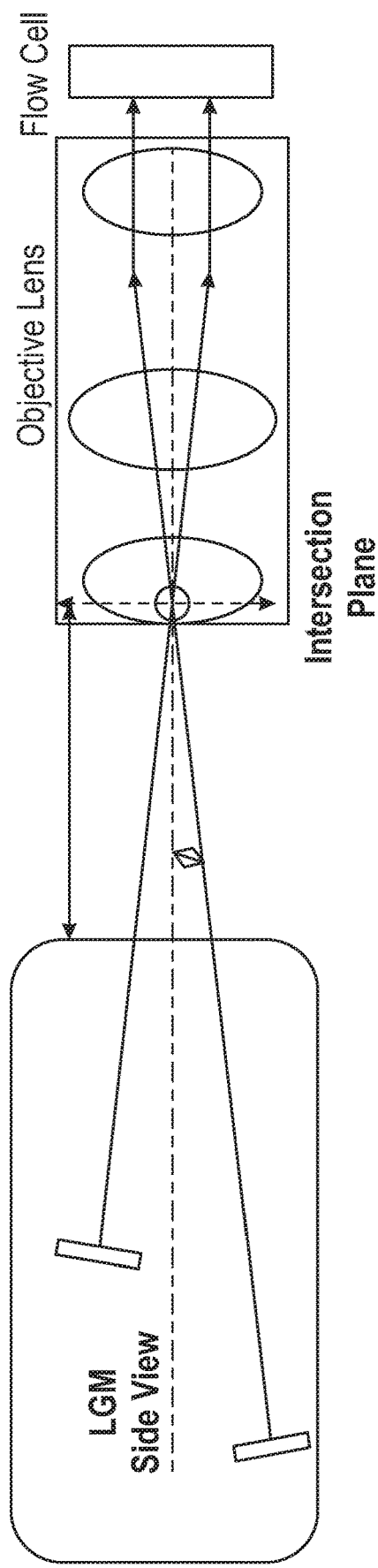
FIG. 1J illustrates a block diagram of an LGM, an objective lens, and flowcell, consistent with implementations disclosed herein.
Figure 1K:
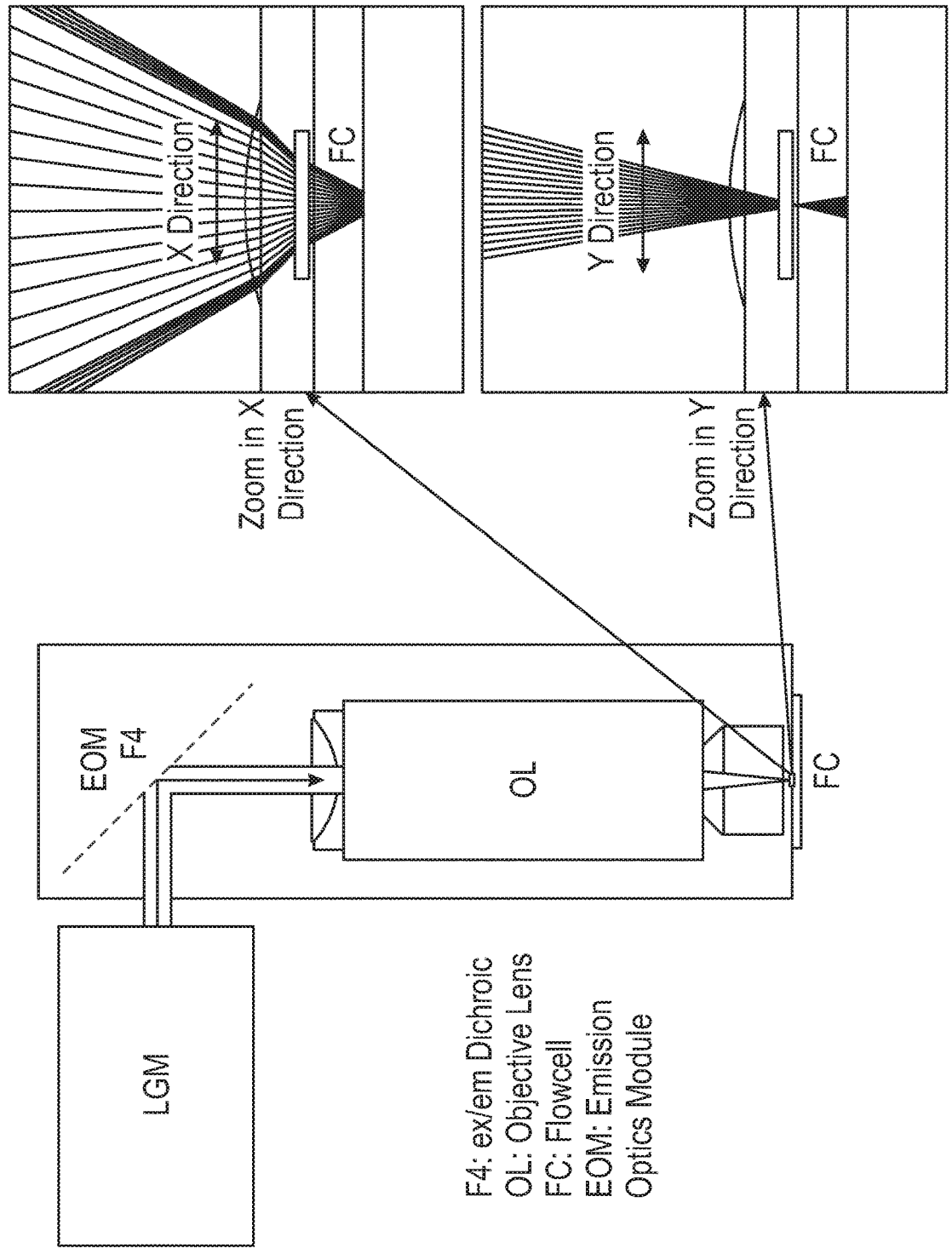
FIG. 1K illustrates a block diagram of an LGM and EOM system used to defocus the laser line pattern on a flowcell to avoid photo-saturation and photo-bleaching, consistent with implementations disclosed herein.

FIG. 1F illustrates a block diagram of a LGM alignment system. FIG. 1G illustrates a perspective view of an LGM alignment system. As illustrated, in some implementations, a green laser module may generate a first laser beam that reflects off two PZT mirrors. Similarly, a red laser module may generate a second laser beam that also reflects off of two PZT mirrors and is combined with the first laser beam. Both laser beams may then pass through a Powell lens to generate a line pattern, and then through a shutter, EOM optics, and an objective lens. In some implementations, the laser beams may be defocused using a defocus lens prior to passing through the objective as to increase the line width of the laser beams. Alternatively, the laser beams may be defocused by articulating the objective in the Z-axis. By focusing the laser beams at a focal point beyond the surfaces of the flowcell, the laser lines may be widened as to disperse energy at the sample and avoid photo-saturation, photo-bleaching, and laser damage at high scanning speeds and high laser powers. In some implementations, the line patterns may be increased in width from less than 5 microns to more than 13 microns.

The LGM alignment system may include control surfaces to adjust or manipulate relative positioning of mirrors 1002 and 1004, as well as the lenses, lasers, or other components or optics in the LGM. For example, adjustments may be made using manual manipulation of control knobs, screws, or other components. In other implementations, one or more of the optical components may be adjusted or manipulated automatically. Automatic control devices may include a motorized translation stage, an actuation device, one or more piezo stages, and/or one or more automatic switch and flip mirrors and lenses. A software interface may be used to control all the devices, test system, calibration, and test procedure. The alignment system includes a beam profiler (e.g., a 2D imaging sensor), imaging lens (replacing EOM objective lens), attenuator, and/or alignment targets. The software interface may be used to output reports for quality control and product evaluation. For example, the reports may include data generated by the beam profiler relating to beam intensity and profile relative to each alignment configuration of the optical components of the LGM.

In some implementations, a method for aligning an LGM using an LGM alignment system may include identifying reasonable alignment positions and tolerances for imaging optics, sensors, and mechanics relative to an LGM alignment system. The LGM alignment system is external to the modular optical analytic system. As such, the internal components of the LGM may be assembled and aligned prior to installation in the modular optical analytic system. The internal components of the LGM may also be aligned during a maintenance activity.

In some implementations, alignment of the LGM optical components may be accomplished using actuated devices for automatic tracking and adjustment during sequencing or between sequencing cycles/runs. For example, the actuated devices can be a piezo stage, a motorized actuator, or similar devices known in the art. The actuated devices may also compensate for drift caused by temperature changes, as well as decay of optical components including lasers, lens, and mounts.

Each optical component may mechanically couple to an enclosure or optical frame using a mechanical interface with precision contact pads, dowel pins, stoppers, or other precision mechanical mounting surfaces as known in the art.

Figure 2A:
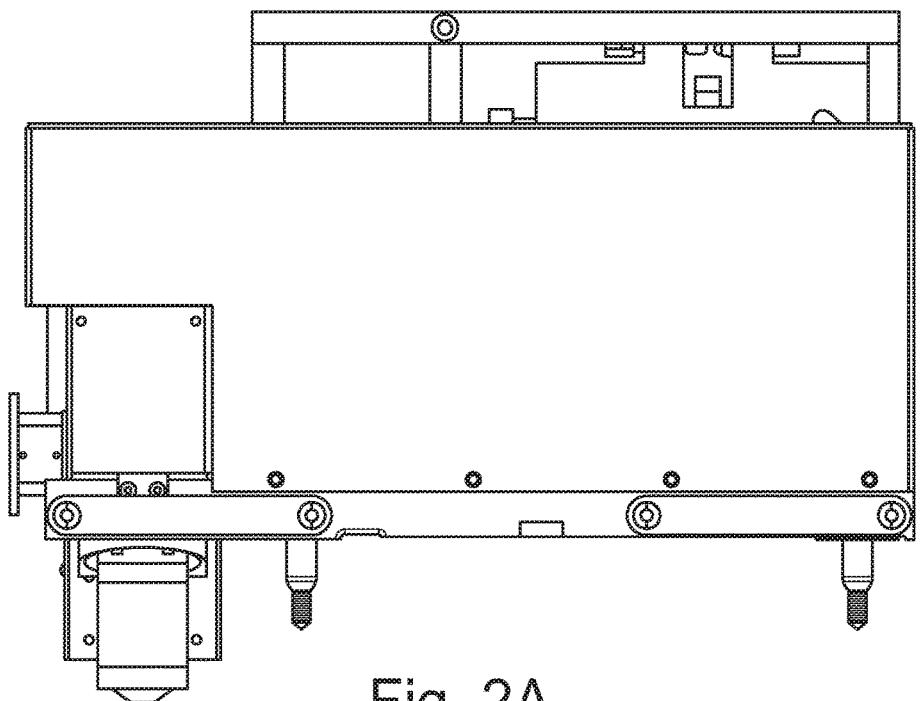
FIG. 2A is a side view diagram illustrating an emission optical module (EOM) in accordance with implementations disclosed herein.
Figure 2B:
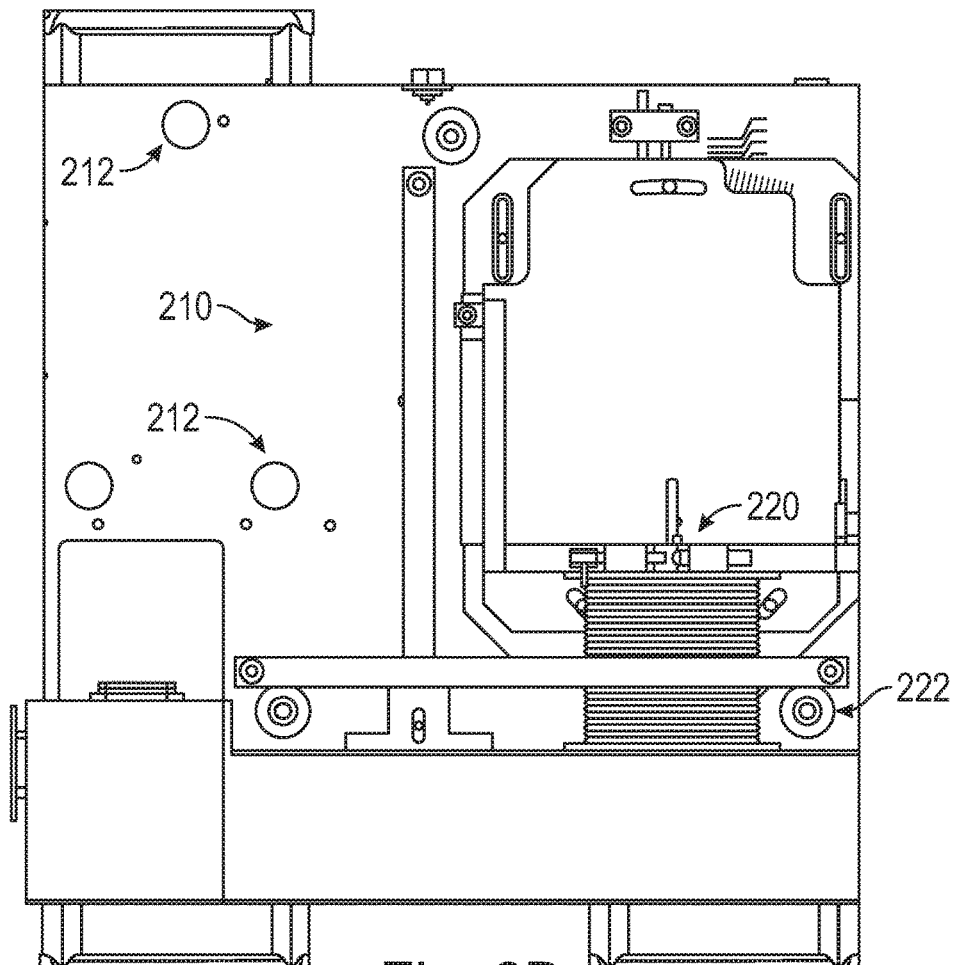
FIG. 2B is a top-down diagram illustrating an EOM in accordance with implementations disclosed herein.

FIGS. 2A and 2B are diagrams illustrating precision mounting structures on EOM 188. In several implementations, EOM 188 may include an EOM enclosure 210. EOM 188 may mechanically and optically couple to LGM 182, FTM 184, and CAM 186 (e.g., the enclosure of EOM 188 may include one or more apertures corresponding to and aligned with an aperture located on an enclosure of each of the other modular subassemblies to enable light, generated by a light source(s) in LGM 182 and/or FTM 184 to transit through the apertures and internal optics of EOM 188.). As illustrated in FIG. 2B, EOM enclosure 210 may include FTM precision mounting structures 212 configured to align and mechanically couple (e.g., physically attach) to corresponding precision mounting structures located on an outer surface of an enclosure of FTM 184. Similarly, EOM enclosure 210 may include CAM mounting structures 222 configured to align and mechanically couple to corresponding precision mounting structures located on an outer surface of an enclosure 220 of CAM 186.

Figure 3B:
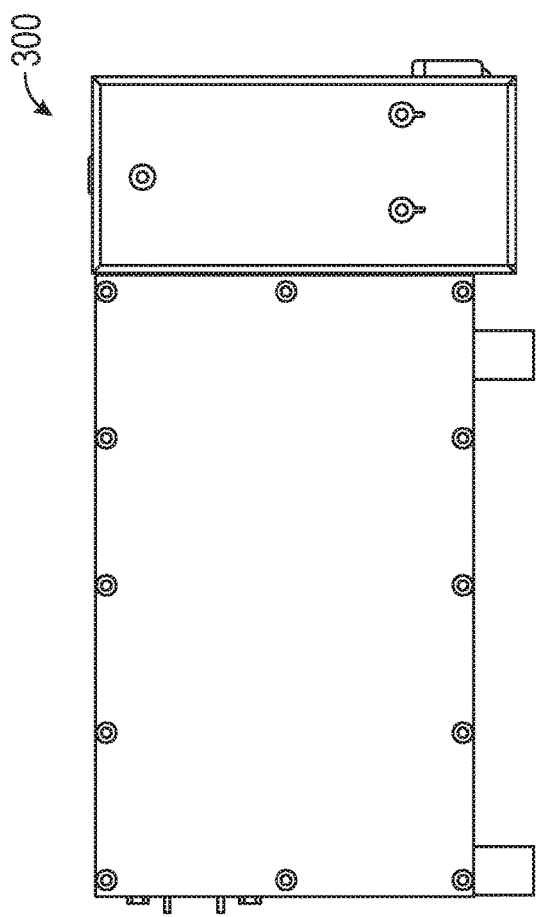
FIG. 3B is a side view diagram illustrating an FTM in accordance with implementations disclosed herein.
Figure 3A:
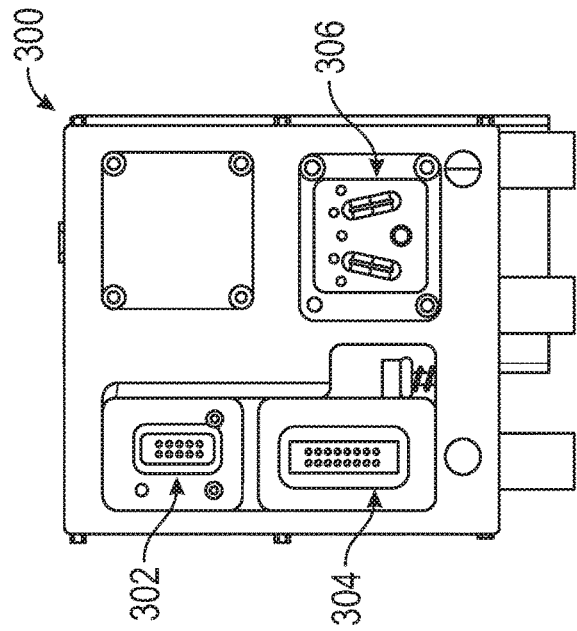
FIG. 3A is a back view diagram illustrating a focus tracking module (FTM) in accordance with implementations disclosed herein.
Figure 3C:
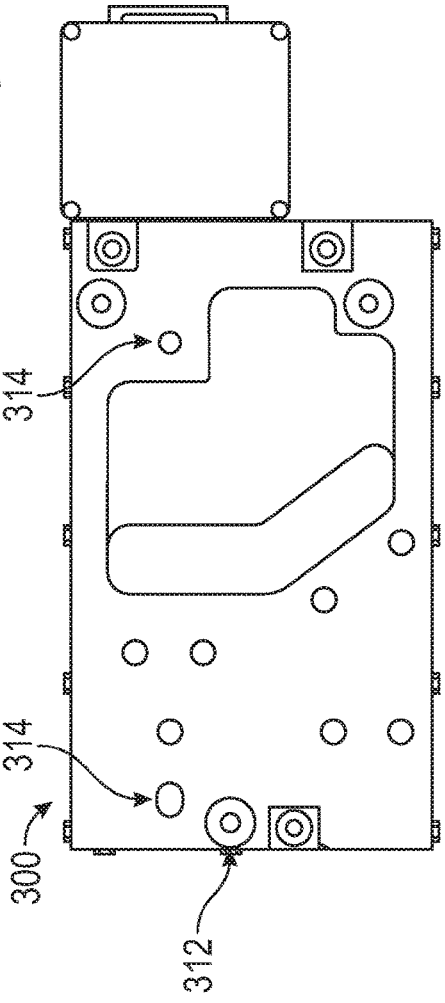
FIG. 3C is a top-down view diagram illustrating an FTM in accordance with implementations disclosed herein.

FIGS. 3A, 3B, and 3C are diagrams illustrating precision mounting structures on FTM 184. Referring to FIG. 3A, FTM 184 may include a light source and optical sensors positioned within FTM enclosure 300. FTM enclosure 300 may include interface ports for electronic interfaces 302, 304, and 306 to control the light source and optical sensors. FTM enclosure 300 may also include precision mounting structures 312 (e.g., precision mounting feet configured to mechanically couple to recesses or predetermined locations on precision mounting plate 190). FTM enclosure 300 may further include precision mounting structures 314 configured to align and mechanically couple to corresponding precision mounting structures 212 located on an outer surface of EOM enclosure 210

Pre-assembling, configuring, aligning, and testing each modular subassembly, and then mounting each to precision mounting plate 190 to assist in system alignment, may reduce the amount of post-installation alignment required to meet desired tolerances. In one example, post installation alignment between EOM 188 and each of the other subassembly modules may be accomplished by interfacing corresponding module ports (e.g., an EOM/FTM port, an EOM/CAM port, and an EOM/LGM port), and aligning the modular subassemblies to each other by manually or automatically articulating the position (in the X, Y, or Z axis), angle (in the X or Y direction), and the rotation of each modular subassembly. Some of the degrees of freedom may be limited by precision alignment structures that predetermine the position and orientation of the modular subassembly with respect to precision mounting plate 190 and adjacent modular subassemblies. Tuning and aligning the internal optics of system 180 may then be accomplished by articulating components internal to the modular subassemblies (e.g., by tilting or moving in either X, Y, or Z mirrors and lenses).

Figure 4A:
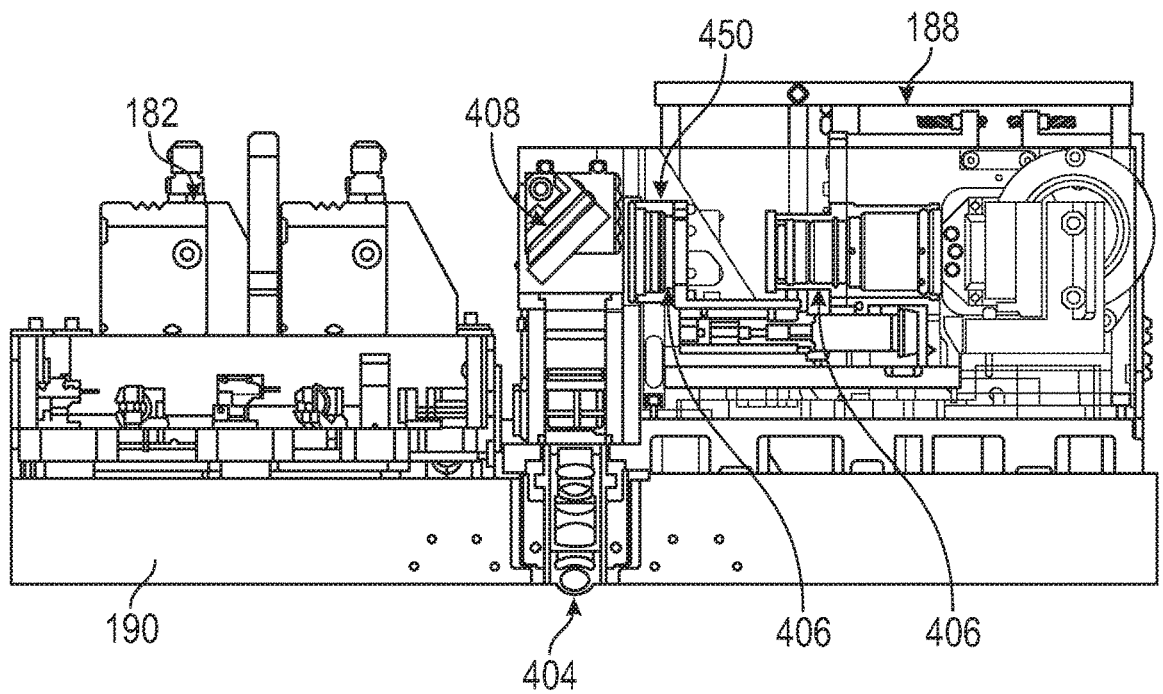
FIG. 4A is a side view diagram illustrating an example modular optical analytic system in accordance with implementations disclosed herein.
Figure 4B:
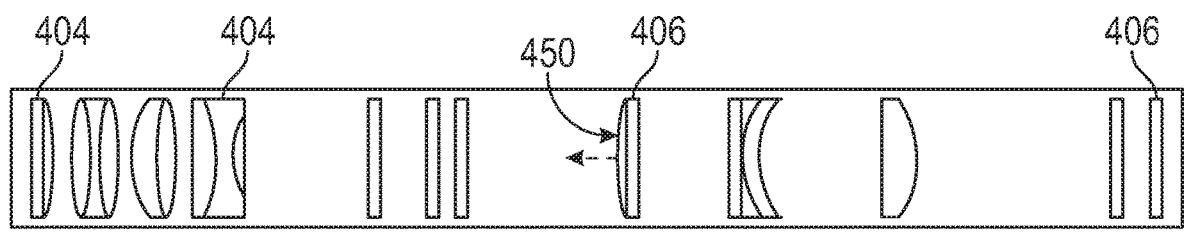
FIG. 4B is a block diagram illustrating an example configuration for a tube lens subassembly from an EOM, in accordance with implementations disclosed herein.
Figure 4C:
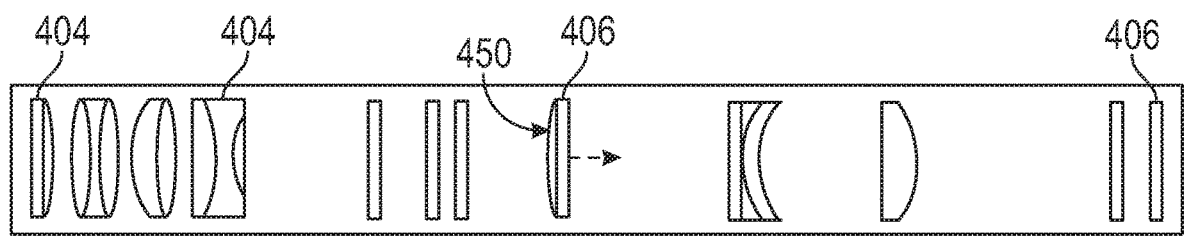
FIG. 4C is a block diagram illustrating another example configuration for a tube lens subassembly from an EOM, in accordance with implementations disclosed herein.

FIG. 4A is a side view diagram illustrating an example modular optical analytic system. As illustrated in FIG. 4A, LGM 182 and EOM 188 may be aligned and mechanically coupled to precision mounting plate 190, as well as to each other. EOM 188 may include an objective 404 aligned, via mirror 408 with tube lens 406, which in turn is optically coupled to LGM 182, such that light beams generated by LGM 182 transmit through an interface baffle between LGM 182 and EOM 188, pass through objective 404, and strike an optical target. Responsive light radiation from the target may then pass back through objective 404 and into tube lens 406. Tube lens 406 may include a lens element 450 configured to articulate along the z-axis to correct for spherical aberration artifacts introduced by objective 404 imaging through varied thickness of flowcell substrate or cover glass. For example, FIGS. 4B and 4C are block diagrams illustrating different configurations of tube lens 406. As illustrated, lens element 450 may be articulated closer to or further away from objective 404 to adjust the beam shape and path.

In some implementations, EOM 188 may be mechanically coupled to a z-stage, e.g., controlled by actuators on alignment stage 192. In some examples, the z-stage may be articulated by a precision coil and actuated by a focusing mechanism which may adjust and moves objective 404 to maintain focus on a flowcell. For example, the signal to control to adjust the focus may be output from FTM 184. This z-stage may align the EOM optics, for example, by articulating objective 404, tube lens 406, and/or lens element 450.

Figure 5A:
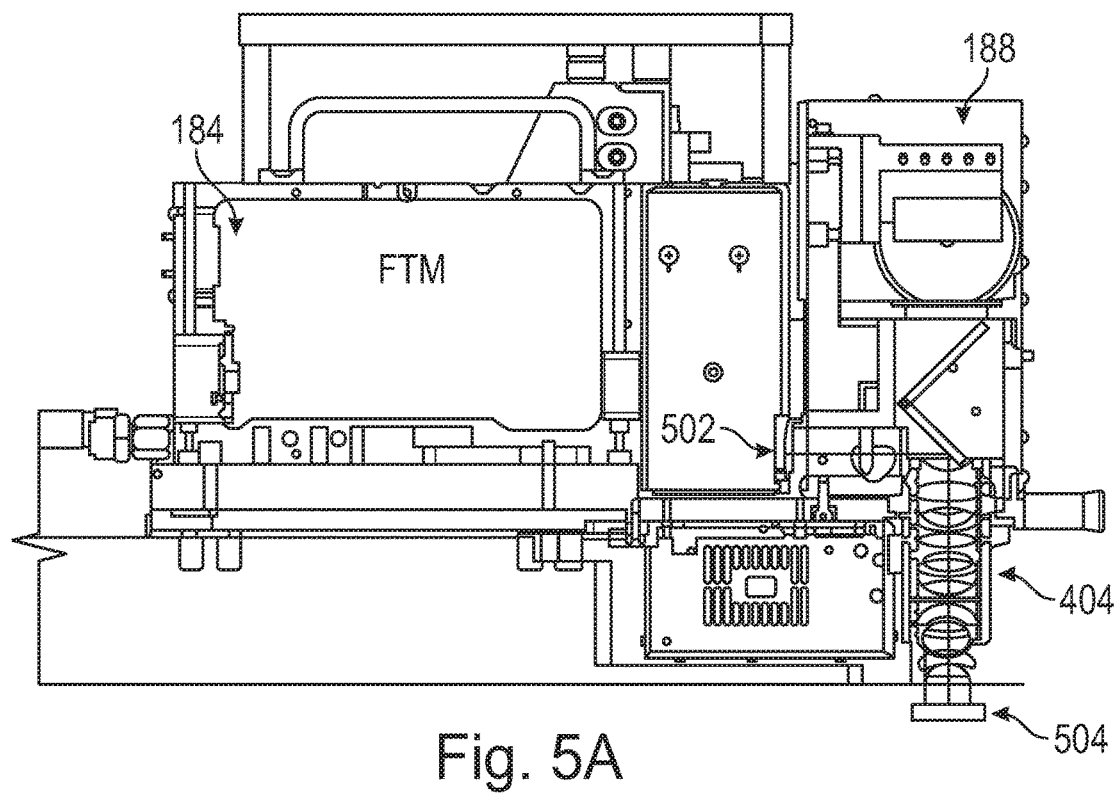
FIG. 5A is a side view diagram illustrating an FTM and an EOM with implementations disclosed herein.
Figure 5B:
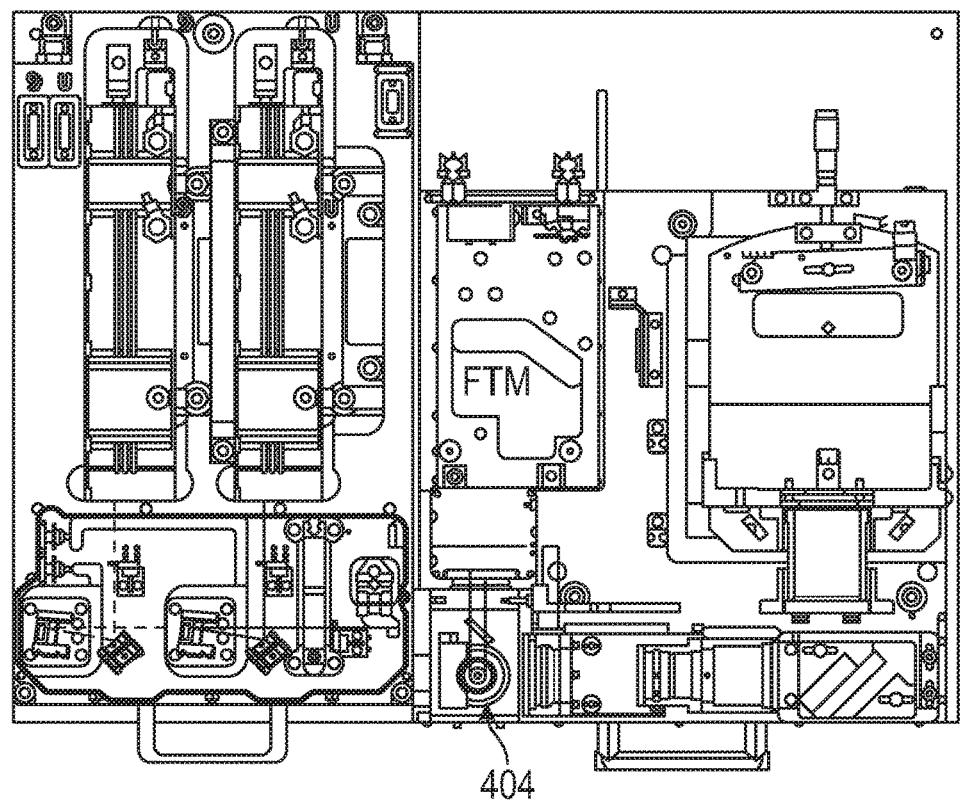
FIG. 5B is a top-down view diagram illustrating an example FTM and an EOM in accordance with implementations disclosed herein.

FIGS. 5A and 5B are diagrams illustrating FTM 184. FTM 184 may interface with EOM 188 through FTM/EOM interface port 502. As illustrated in FIG. 5A, light beams originating in FTM 184 and passing through the optics of EOM 188 may reflect off flowcell 504. As disclosed herein, FTM 184 may be configured to provide feedback to a computer processor in order to control alignment and positioning of optical components throughout system 180. For example, FTM 184 may employ a focus mechanism using two or more parallel light beams which pass through objective 404 and reflect off flowcell 504. Movement of the flowcell away from an optimal focus position may cause the reflected beams to change angle as they exit objective 404. That angle may be measured by an optical sensor located in FTM 184. In some examples, the distance of the light path between the optical sensor surface and the objective 404 may be between 300 mm and 700 mm distance. FTM 184 may initiate a feedback loop using an output signal from the optical sensor to maintain a pre-determined lateral separation between beam spot patterns of the two or more parallel light beams by adjusting the position of objective 404 using the z-stage in the EOM.

Some implementations of system 180 provide a compensation method for top and bottom surface imaging of flowcell 504. In some examples, flowcell 504 may include a cover glass layered on a layer of liquid and a substrate. For example, the cover glass may be between about 100 um and about 500 um thick, the liquid layer may be between about 50 um and about 150 um thick, and the substrate may be between about 0.5 and about 1.5 mm thick. In one example, a DNA sample may be introduced at the top and bottom of the liquid channel (e.g., at the top of the substrate, and bottom of the cover glass). To analyze the sample, the focal point of the incident light beams at various depths of flowcell 504 may be adjusted by moving the z-stage (e.g., to focus on the top of the substrate or the bottom of the cover glass. Movement of objective 404 to change incident beam focal points within flowcell 504 may introduce imaging artifacts or defects, such as spherical aberration. To correct for these artifacts or defects, lens element 450 within tube lens 406 may be moved closer to or further away from objective 404.

In some examples FTM 184 may be configured as a single FRU with no replaceable internal components. To increase longevity and reliability of FTM internal components, such as the laser, laser output may be reduced (for example, below 5 mW).

Figure 6:
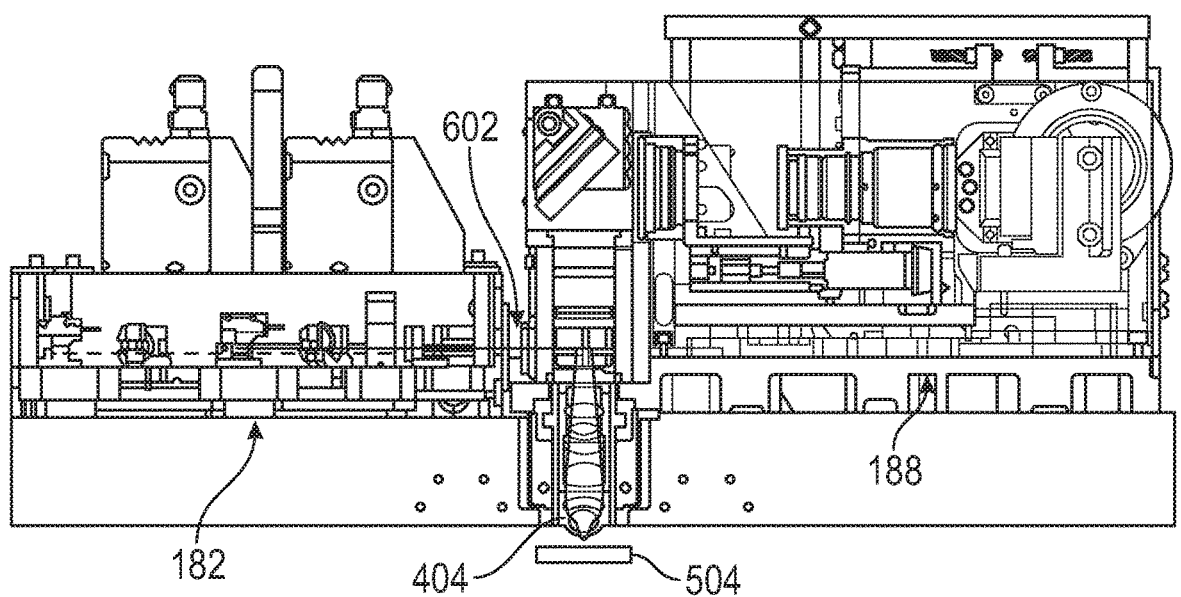
FIG. 6 is a side view diagram illustrating a line generation module (LGM) and an EOM in accordance with implementations disclosed herein.
Figure 7:
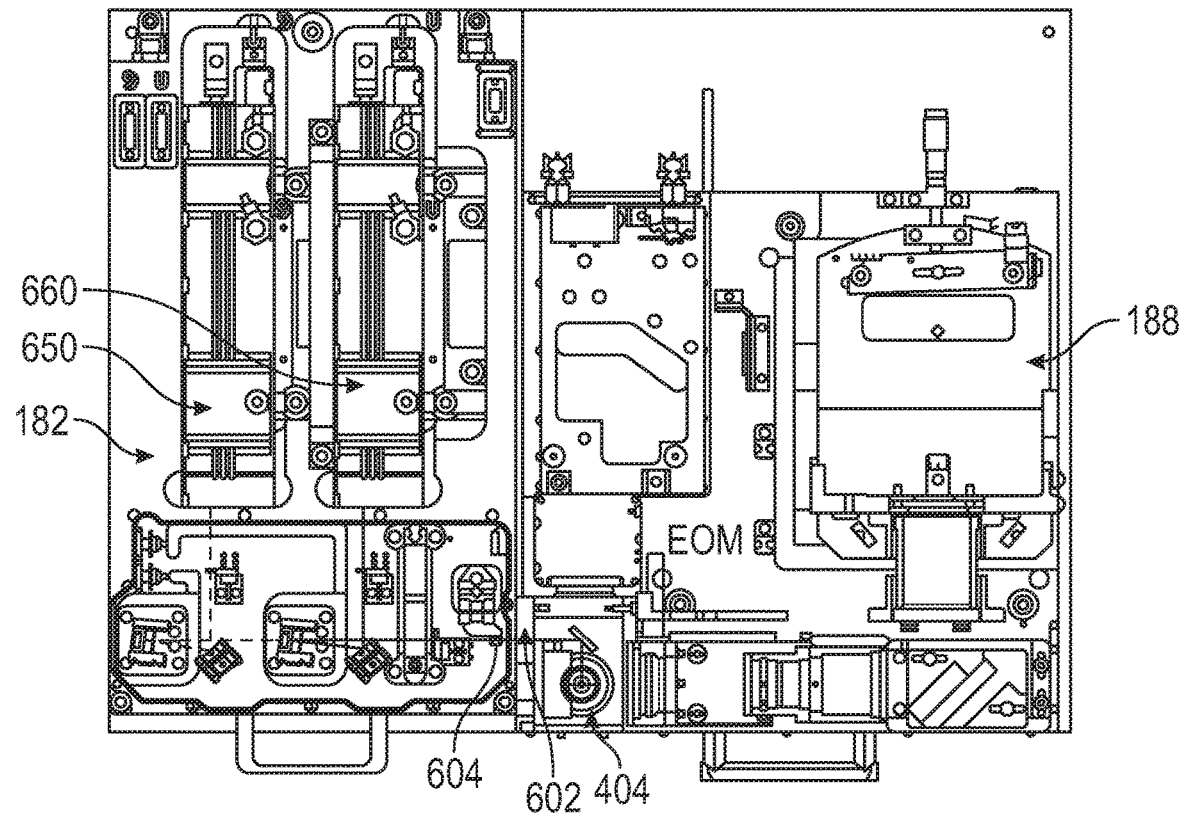
FIG. 7 is a top-down view diagram illustrating an LGM and an EOM in accordance with implementations disclosed herein.

FIGS. 6 and 7 are diagrams illustrating LGM 182 and EOM 188. As illustrated, LGM 182 may interface with EOM 188 through LGM/EOM interface baffle 602. LGM 182 is a photon source for system 180. One or more light sources (e.g., light sources 650 and 660) may be positioned within an enclosure of LGM 182. Light generated from light sources 650 and 660 may be directed through a beam shaping lens 604 and into the optical path of EOM 188 through LGM/EOM interface baffle 602. For example, light source 650 may be a green laser and light source 660 may be a red laser. The lasers may operate at high powers (e.g., more than 3 Watts). One or more beam shaping lenses 604 may be implemented to shape the light beams generated from the light sources into desired shapes (e.g., a line).

Photons generated by light sources 650 and 660 (e.g., green wavelength photons and red wavelength photons) may excite fluorophores in DNA located on flowcell 504 to enable analysis of the base pairs present within the DNA. High speed sequencing employs high velocity scanning to deliver a sufficient photon dose to the DNA fluorophores, to stimulate sufficient emission of reactive photons from the DNA sample to be detected by the light sensors in CAM 186.

Beam shaping lens 604 may be a Powell lens that spreads the Gaussian light emitted by lasers 650 and 660 into a uniform profile (in longitudinal direction), which resembles a line. In some example implementations, a single beam shaping 604 lens may be used for multiple light beams (e.g., both a red and a green light beam) which may be incident on the front of beam shaping lens 604 at different pre-determined angles (e.g., plus or minus a fraction of a degree) to generate a separate line of laser light for each incident laser beam. The lines of light may be separated by a pre-determined distance to enable clear detection of separate signals, corresponding to each light beam, by the multiple optical sensors in CAM 186. For example, a green light beam may ultimately be incident on a first optical sensor in CAM 186 and a second light beam may ultimately be incident on a second optical sensor in CAM 186.

In some examples, the red and green light beams may be coincident/superimposed as they enter beam shaping lens 604 and then begin to fan out into respective line shapes as they reach objective 404. The position of the beam shaping lens may be controlled with tight tolerance near or in close proximity to light sources 650 and 660 to control beam divergence and optimize shaping of the light beams, i.e., by providing sufficient beam shape (e.g., length of the line projected by the light beam) while still enabling the entire beam shape to pass through objective 404 without clipping any light. In some examples, distance between beam shaping lens 604 and objective 404 is less than about 150 mm.

In some implementations, system 180 may further comprise a modular subassembly having a pocket to receive the optical target. The body may comprise aluminum that includes a pigment having a reflectivity of no more than about 6.0%. The body may include an inset region located at the top surface and surrounding the pocket. The modular subassembly may further comprise a transparent grating layer mounted in the inset region and may be positioned above the optical target and spaced apart from the optical target by a fringe gap. The body may include a pocket to receive the optical target. The body may include a diffusion well located below the optical target. The diffusion well may receive excitation light passing through the optical target. The diffusion well may include a well bottom having a pigment based finish that exhibits a reflectively of no more than about 6.0%.

One of the modular subassemblies of system 180 may further include an optical detection device. Objective 404 may emit excitation light toward the optical target and receive fluorescence emission from the optical target. An actuator may be configured to position objective 404 to a region of interest proximate to the optical target. The processor may then execute program instructions for detecting fluorescence emission from the optical target in connection with at least one of optical alignment and calibration of an instrument.

In some examples, objective 404 may direct excitation light onto the optical target. The processor may derive reference information from the fluorescence emission. The processor may utilize the reference information in connection with the at least one of optical alignment and calibration of the instrument. The optical target may be permanently mounted at a calibration location proximate to objective 404. The calibration location may be separate from flowcell 504. The solid body may represent a substrate comprising a solid host material with the fluorescing material embedded in the host material. The solid body may represent at least one of an epoxy or polymer that encloses quantum dots that emit fluorescence in one or more predetermined emission bands of interest when irradiated by the excitation light.

Figure 8:
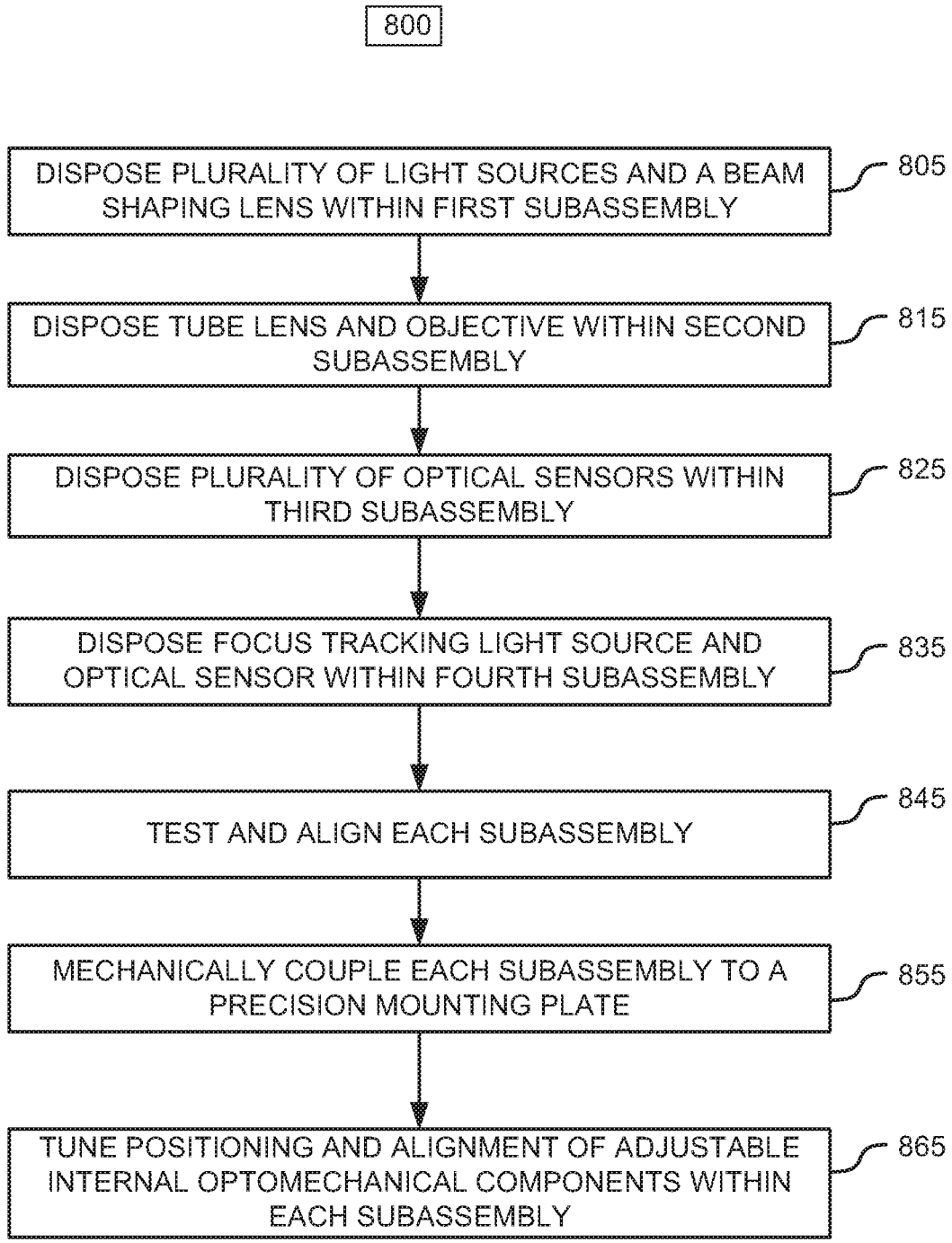
FIG. 8 is a diagram illustrating an example process for installing and configuring a modular optical analytic system in accordance with implementations disclosed herein.

FIG. 8 is a diagram illustrating an example process for installing and configuring a modular optical analytic system 800. Process 800 may include positioning a plurality of light sources and a beam shaping lens within a first subassembly at step 805. For example, the plurality of light sources may include light source 650 and light source 660. The first subassembly may be an LGM, which may include an LGM enclosure to which the light sources are mounted and aligned. The beam shaping lens may be a Powell lens, also mounted within the LGM enclosure, and configured to shape light beams generated by light sources 650 and 660 into separate line patterns.

Process 800 may also include positioning a tube lens and objective within a second subassembly at step 815. For example, the second subassembly may be an EOM and may include an EOM enclosure to which the objective and tube lens are mounted and aligned.

Process 800 may also include positioning a plurality of optical sensors within a third subassembly at step 825. For example, the third subassembly may be a CAM and may include a CAM enclosure to which the optical sensors are aligned and mounted. There may be a corresponding optical sensor to each light source from step 805.

Process 800 may also include positioning a focus tracking light source and optical sensor within a fourth subassembly at step 835. For example, the fourth subassembly may be an FTM and may include an FTM enclosure to which the focus tracking light source and optical sensor are mounted.

In some implementations, process 800 may further include individually testing each subassembly at step 845. For example, testing may include precisely tuning and/or aligning the internal components of each subassembly to the subassembly's enclosure. Each subassembly may then be mechanically coupled to a precision mounting plate at step 855. For example, the precision mounting plate may be precision mounting plate 190. The entire system may then be aligned and tuned by powering the focus tracking light source in the fourth subassembly and capturing an output signal from the focus tracking optical sensor of the fourth subassembly to find an optimal focus of the optical target. The output signal from the target may be input into a computer processor configured to analyze the characteristics of light beams generated by the focus tracking light source, and then provide feedback to actuators on one or more of the subassemblies, or to a graphical user interface to enable tuning of the optical components to optimize beam shape, power, and focus.

As noted above, in various implementations an actuator can be used to position the sample stage relative to the optical stage by repositioning either the sample stage or the optical stage (or parts thereof), or both to achieve the desired focus setting. In some implementations, piezoelectric actuators can be used to move the desired stage. In other implementations, a voice coil actuator can be used to move the desired stage. In some applications, the use of a voice coil actuator can provide reduced focusing latency as compared to its piezoelectric counterparts. For implementations using a voice coil actuator, coil size may be chosen as a minimum coil size needed to provide the desired movement such that the inductance in the coil can also be minimized. Limiting coil size, and therefore limiting its inductance, provides quicker reaction times and requires less voltage to drive the actuator.

As described above, regardless of the actuator used, focus information from points other than a current sample location can be used to determine the slope or the magnitude of change in the focus setting for scanning operations. This information can be used to determine whether to feed the drive signal to the actuator earlier and how to set the parameters of the drive signal. Additionally, in some implementations the system can be pre-calibrated to allow drive thresholds to be determined for the actuator. For example, the system can be configured to supply to the actuator drive signals at different levels of control output to determine the highest amount of control output (e.g., the maximum amount of drive current) the actuator can withstand without going unstable. This can allow the system to determine a maximum control output amount to be applied to the actuator.

Figure 9:
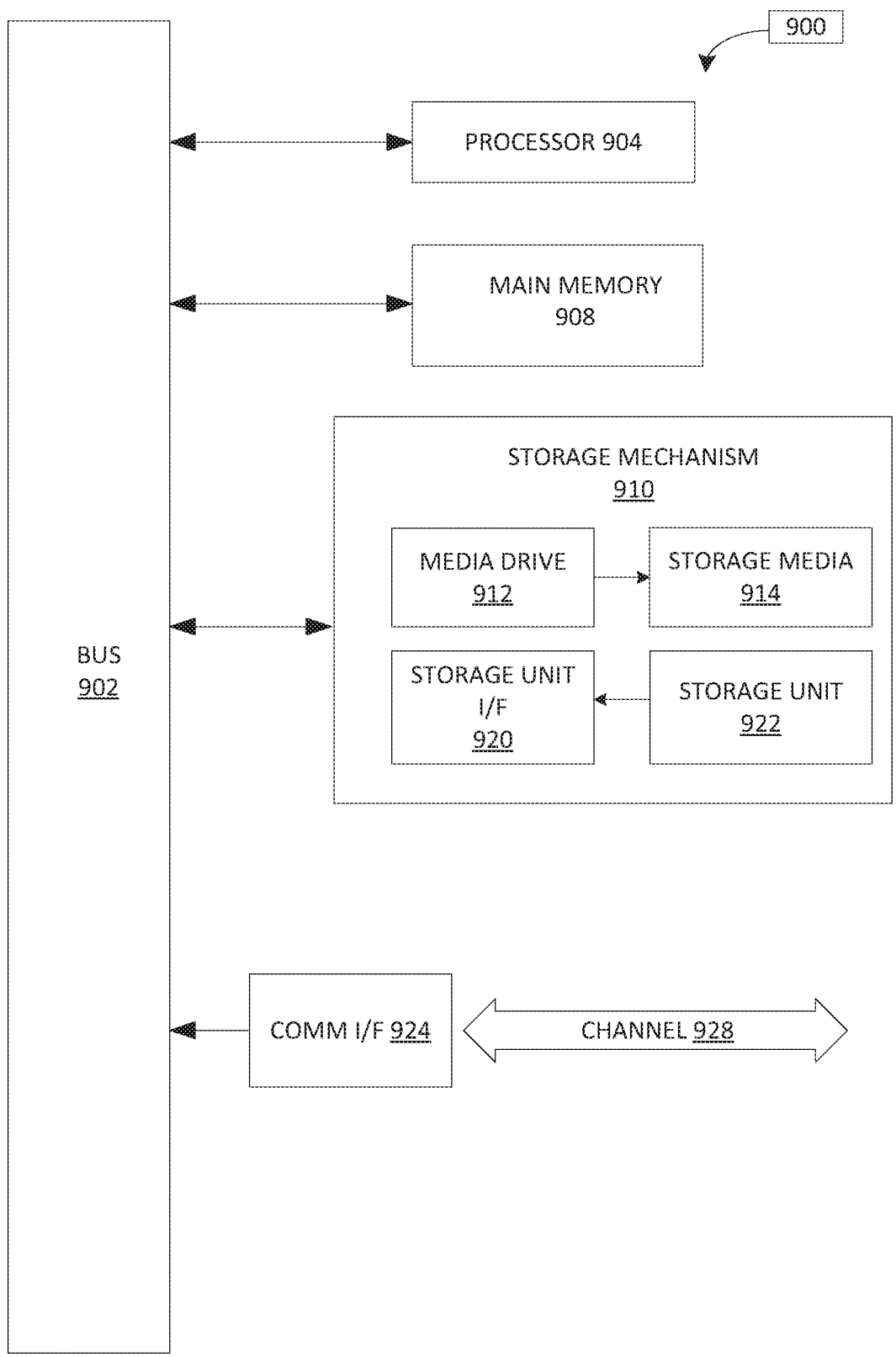
FIG. 9 illustrates an example computing engine that may be used in implementing various features of implementations of the disclosed technology.

As used herein, the term engine may describe a given unit of functionality that can be performed in accordance with one or more implementations of the technology disclosed herein. As used herein, an engine may be implemented utilizing any form of hardware, software, or a combination thereof. For example, one or more processors, controllers, ASICs, PLAs, PALs, CPLDs, FPGAs, logical components, software routines or other mechanisms may be implemented to make up an engine. In implementation, the various engines described herein may be implemented as discrete engines or the functions and features described can be shared in part or in total among one or more engines. In other words, as would be apparent to one of ordinary skill in the art after reading this description, the various features and functionality described herein may be implemented in any given application and can be implemented in one or more separate or shared engines in various combinations and permutations. Even though various features or elements of functionality may be individually described or claimed as separate engines, one of ordinary skill in the art will understand that these features and functionality can be shared among one or more common software and hardware elements, and such description shall not require or imply that separate hardware or software components are used to implement such features or functionality.

Where components or engines of the technology are implemented in whole or in part using software, in one implementation, these software elements can be implemented to operate with a computing or processing engine capable of carrying out the functionality described with respect thereto. One such example computing engine is shown in FIG. 9. Various implementations are described in terms of this example computing engine 900. After reading this description, it will become apparent to a person skilled in the relevant art how to implement the technology using other computing engines or architectures.

Referring now to FIG. 9, computing engine 900 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Computing engine 900 may also represent computing capabilities embedded within or otherwise available to a given device. For example, a computing engine may be found in other electronic devices such as, for example, digital cameras, navigation systems, cellular telephones, portable computing devices, modems, routers, WAPs, terminals and other electronic devices that may include some form of processing capability.

Computing engine 900 may include, for example, one or more processors, controllers, control engines, or other processing devices, such as a processor 904. Processor 904 may be implemented using a general-purpose or special-purpose processing engine such as, for example, a microprocessor, controller, or other control logic. In the illustrated example, processor 904 is connected to a bus 902, although any communication medium can be used to facilitate interaction with other components of computing engine 900 or to communicate externally.

Computing engine 900 may also include one or more memory engines, simply referred to herein as main memory 908. For example, preferably random access memory (RAM) or other dynamic memory, may be used for storing information and instructions to be executed by processor 904. Main memory 908 may also be used for storing temporary variables or other intermediate information during execution of instructions to be executed by processor 904. Computing engine 900 may likewise include a read only memory ("ROM") or other static storage device coupled to bus 902 for storing static information and instructions for processor 904.

The computing engine 900 may also include one or more various forms of information storage mechanism 910, which may include, for example, a media drive 912 and a storage unit interface 920. The media drive 912 may include a drive or other mechanism to support fixed or removable storage media 914. For example, a hard disk drive, a floppy disk drive, a magnetic tape drive, an optical disk drive, a CD or DVD drive (R or RW), or other removable or fixed media drive may be provided. Accordingly, storage media 914 may include, for example, a hard disk, a floppy disk, magnetic tape, cartridge, optical disk, a CD or DVD, or other fixed or removable medium that is read by, written to or accessed by media drive 912. As these examples illustrate, the storage media 914 can include a computer usable storage medium having stored therein computer software or data.

In alternative implementations, information storage mechanism 910 may include other similar instrumentalities for allowing computer programs or other instructions or data to be loaded into computing engine 900. Such instrumentalities may include, for example, a fixed or removable storage unit 922 and an interface 920. Examples of such storage units 922 and interfaces 920 can include a program cartridge and cartridge interface, a removable memory (for example, a flash memory or other removable memory engine) and memory slot, a PCMCIA slot and card, and other fixed or removable storage units 922 and interfaces 920 that allow software and data to be transferred from the storage unit 922 to computing engine 900.

Computing engine 900 may also include a communications interface 924. Communications interface 924 may be used to allow software and data to be transferred between computing engine 900 and external devices. Examples of communications interface 924 may include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 924 may be carried on signals, which can be electronic, electromagnetic (which includes optical) or other signals capable of being exchanged by a given communications interface 924. These signals may be provided to communications interface 924 via a channel 928. This channel 928 may carry signals and may be implemented using a wired or wireless communication medium. Some examples of a channel may include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 908, storage unit 922, media 914, and channel 928. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions may enable the computing engine 900 to perform features or functions of the disclosed technology as discussed herein.

While various implementations of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent engine names other than those depicted herein can be applied to the various partitions. Additionally, with regard to flow diagrams, operational descriptions and method claims, the order in which the steps are presented herein shall not mandate that various implementations be implemented to perform the recited functionality in the same order unless the context dictates otherwise.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. For example, although the disclosed technology is described above in terms of various example implementations, it should be understood that the various features, aspects and functionality described in one or more of the individual implementations are not limited in their applicability to the particular implementation with which they are described, but instead can be applied, alone or in various combinations, to one or more of the other implementations of the disclosed technology, whether or not such implementations are described and whether or not such features are presented as being a part of a described implementation. Thus, the breadth and scope of the technology disclosed herein should not be limited by any of the above-described example implementations.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide example instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

To the extent applicable, the terms "first," "second," "third," etc. herein are merely employed to show the respective objects described by these terms as separate entities and are not meant to connote a sense of chronological order, unless stated explicitly otherwise herein.

The term "coupled" refers to direct or indirect joining, connecting, fastening, contacting or linking, and may refer to various forms of coupling such as physical, optical, electrical, fluidic, mechanical, chemical, magnetic, electromagnetic, communicative or other coupling, or a combination of the foregoing. Where one form of coupling is specified, this does not imply that other forms of coupling are excluded. For example, one component physically coupled to another component may reference physical attachment of or contact between the two components (directly or indirectly), but does not exclude other forms of coupling between the components such as, for example, a communications link (e.g., an RF or optical link) also communicatively coupling the two components. Likewise, the various terms themselves are not intended to be mutually exclusive. For example, a fluidic coupling, magnetic coupling or a mechanical coupling, among others, may be a form of physical coupling.

The presence of broadening words and phrases such as "one or more," "at least," "but not limited to" or other like phrases in some instances shall not be read to mean that the narrower case is intended or required in instances where such broadening phrases may be absent. The use of the term "engine" does not imply that the components or functionality described or claimed as part of the engine are all configured in a common package. Indeed, any or all of the various components of an engine, whether control logic or other components, can be combined in a single package or separately maintained and can further be distributed in multiple groupings or packages or across multiple locations.

Additionally, the various implementations set forth herein are described in terms of exemplary block diagrams, flow charts and other illustrations. As will become apparent to one of ordinary skill in the art after reading this document, the illustrated implementations and their various alternatives can be implemented without confinement to the illustrated examples. For example, block diagrams and their accompanying description should not be construed as mandating a particular architecture or configuration.

We claim:

1. An imaging system, comprising:
   an objective lens; and
   a line generation device, comprising:
   a first light source to emit a first light beam at a first wavelength;

a second light source to emit a second light beam at a second wavelength; and
one or more line forming optics to shape a light beam emitted by the first light source into a line and a light beam emitted by the second light source into a line;
wherein the objective lens is to focus the first light beam and the second light beam at a focal point external to a sampling structure; and
wherein a line width of the first light beam is increased to lower overall power density of the first light beam on a surface of the sampling structure such that the power density of the first light beam on the surface of the sampling structure is below a photosaturation threshold of a first dye of a sample.

2. The imaging system of claim 1, wherein the sampling structure comprises a cover plate, a substrate, and a liquid passage between the cover plate and substrate, wherein the liquid passage comprises a top interior surface and a bottom interior surface, wherein the sample is located at the top interior surface or at the bottom interior surface of the liquid passage.

3. The imaging system of claim 2, further comprising: a time delay integration (TDI) sensor to detect fluorescence emissions from the sample, wherein the TDI sensor has a pixel size between about 5 μm and about 15 μm, a sensor width between about 0.4 mm and about 0.8 mm, and a sensor length between about 16 mm and about 48 mm.

4. The imaging system of claim 3, further comprising: a z-stage for articulating the objective to adjust the line width of the first light beam and to adjust the line width of the second light beam.

5. The imaging system of claim 4, further comprising:
a processor; and
a non-transitory computer readable medium with computer executable instructions embedded thereon, the computer executable instructions configured to cause the imaging system to:
determine a quality of a signal from the TDI sensor; and
articulate the objective in the z-axis to adjust the focal point and optimize the quality of the signal from the TDI sensor.

6. The imaging system of claim 2, wherein the line width of the first light beam and the line width of the second light beam is between about 10 μm and about 30 μm.

7. The imaging system of claim 2, further comprising a one or more line widening optics to increase the line width of the first light beam and the line width of the second light beam.

8. The imaging system of claim 7, wherein the one or more line widening optics comprises defocus lens, a prism, or a diffuser.

9. The imaging system of claim 1, further comprising: at least one optical sensor, wherein the objective lens focuses a focal point for the at least one optical sensor within the sampling structure.

10. The imaging system of claim 1, wherein the imaging system is a DNA sequencing system, wherein the sampling structure is a flow cell.

11. The imaging system of claim 10, wherein the focal point is above a top interior surface of the flow cell or below a bottom interior surface of the flow cell.

12. The imaging system of claim 11, wherein the focal point is between about 50 μm and about 150 μm below the bottom interior surface of the flow cell or between about 50 μm and about 150 μm above the top interior surface of the flow cell.

13. An imaging system, comprising:
an objective lens; and
a line generation device, comprising:
a first light source to emit a first light beam at a first wavelength;
a second light source to emit a second light beam at a second wavelength; and
one or more line forming optics to shape a light beam emitted by the first light source into a line and a light beam emitted by the second light source into a line;
wherein the objective lens is to focus the first light beam and the second light beam at a focal point external to a sample of a sampling structure, the sampling structure comprising a cover plate, a substrate, and a liquid passage between the cover plate and substrate, wherein the liquid passage comprises a top interior surface and a bottom interior surface, wherein the sample is located at the top interior surface or at the bottom interior surface of the liquid passage; and
wherein the focal point is below the bottom interior surface of the liquid passage to increase a line width of the first light beam and a line width of the second line beam at the top interior surface of the sampling structure.

14. The imaging system of claim 13, wherein the focal point is between about 50 μm and about 150 μm below the bottom interior surface of the sampling structure.

15. The imaging system of claim 14, wherein the line length of the first light beam and the line length of the second light is between about 1 mm and about 1.5 mm.

16. An imaging system, comprising:
an objective lens; and
a line generation device, comprising:
a first light source to emit a first light beam at a first wavelength;
a second light source to emit a second light beam at a second wavelength; and
one or more line forming optics to shape a light beam emitted by the first light source into a line and a light beam emitted by the second light source into a line;
wherein the objective lens is to focus the first light beam and the second light beam at a focal point external to a sample of a sampling structure, the sampling structure comprising a cover plate, a substrate, and a liquid passage between the cover plate and substrate, wherein the liquid passage comprises a top interior surface and a bottom interior surface, wherein the sample is located at the top interior surface or at the bottom interior surface of the liquid passage; and
wherein the focal point is above the top interior surface of the liquid passage as to increase a line width of the first light beam and a line width of the second line beam at the top interior surface of the sampling structure.

17. The imaging system of claim 16, wherein the focal point is between about 50 μm and about 150 μm above the top interior surface of the sampling structure.

18. The imaging system of claim 17, wherein the line length of the first light beam and the line length of the second light is between about 1 mm and about 1.5 mm.

19. An imaging system, comprising:
an objective lens;
a line generation device, comprising:
a first light source to emit a first light beam at a first wavelength;
a second light source to emit a second light beam at a second wavelength; and one or more line forming optics to shape a light beam emitted by the first light source into a line and a light beam emitted by the second light source into a line; and one or more line widening optics to increase the line width of the first light beam and the line width of the second light beam, the one or more line widening optics comprising a Powell lens positioned after a defocus lens in an optical path from the first light source and second light source to the objective lens; and wherein the objective lens is to focus the first light beam and the second light beam at a focal point external to a sample of a sampling structure.

20. An imaging system, comprising:

an objective lens; and a line generation device, comprising:

a first light source to emit a first light beam at a first wavelength;

a second light source to emit a second light beam at a second wavelength; and one or more line forming optics to shape a light beam emitted by the first light source into a line and a light beam emitted by the second light source into a line;

wherein the objective lens is to focus the first light beam and the second light beam at a focal point external to a sample of a sampling structure; and wherein a line width of the first light beam is increased to lower overall power density of the first light beam on a surface of the sample such that the power density of the first light beam on the surface of the sample is below a photosaturation threshold of a first dye on the sample, and wherein a line width of the second light beam is increased to lower overall power density of the second light beam on a surface of the sample such that the power density of the second light beam on the surface of the sample is below a photosaturation threshold of a second dye on the sample.

* * * * *